(12) United States Patent
Li et al.

(10) Patent No.: US 11,001,840 B2
(45) Date of Patent: May 11, 2021

(54) BIODEGRADABLE AND CLINICALLY-COMPATIBLE NANOPARTICLES AS DRUG DELIVERY CARRIERS

(71) Applicant: 1Globe Health Institute LLC, Norwood, MA (US)

(72) Inventors: Chiang Jia Li, Cambridge (CA); Youzhi Li, Norwood, MA (US); Keyur Gada, Norwood, MA (US); Xiaoshu Dai, Norwood, MA (US)

(73) Assignee: 1GLOBE HEALTH INSTITUTE LLC, Norwood, MA (US)

( * ) Notice: Subject to any disclaimer, the term of this patent is extended or adjusted under 35 U.S.C. 154(b) by 0 days.

(21) Appl. No.: 14/765,763

(22) PCT Filed: Feb. 5, 2014

(86) PCT No.: PCT/US2014/014751
§ 371 (c)(1),
(2) Date: Oct. 16, 2015

(87) PCT Pub. No.: WO2014/123935
PCT Pub. Date: Aug. 14, 2014

(65) Prior Publication Data
US 2016/0046936 A1 Feb. 18, 2016

Related U.S. Application Data

(60) Provisional application No. 61/761,012, filed on Feb. 5, 2013.

(51) Int. Cl.
*C12N 15/113* (2010.01)
*A61K 9/107* (2006.01)
*A61K 9/51* (2006.01)
*C07K 16/00* (2006.01)
*A61K 38/38* (2006.01)
*C12N 15/11* (2006.01)
*A61K 47/69* (2017.01)

(52) U.S. Cl.
CPC .......... *C12N 15/113* (2013.01); *A61K 9/5115* (2013.01); *A61K 9/5146* (2013.01); *A61K 9/5169* (2013.01); *A61K 38/38* (2013.01); *A61K 47/6923* (2017.08); *C07K 16/00* (2013.01); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 5,219,577 A | 6/1993 | Kossovsky | |
| 5,504,102 A * | 4/1996 | Agharkar | A61K 9/0019 514/449 |
| 5,879,715 A * | 3/1999 | Higgins | B01D 61/145 423/659 |
| 6,555,376 B2 * | 4/2003 | Maitra | A61K 47/48092 435/458 |
| 7,982,027 B2 | 7/2011 | MacLachlan et al. | |
| 8,956,572 B2 | 2/2015 | Knopov et al. | |
| 9,079,874 B2 | 7/2015 | Sugimoto et al. | |
| 2008/0248108 A1 * | 10/2008 | Krotz | A61K 9/1652 424/463 |
| 2009/0011008 A1 | 1/2009 | Sung et al. | |
| 2009/0208564 A1 * | 8/2009 | Li | C12N 15/111 424/450 |
| 2010/0204303 A1 | 8/2010 | Murthy et al. | |
| 2010/0286378 A1 | 11/2010 | Li et al. | |
| 2011/0038939 A1 * | 2/2011 | Lvov | A61K 9/5138 424/490 |
| 2011/0038941 A1 | 2/2011 | Lee et al. | |
| 2011/0065781 A1 | 3/2011 | Sugimoto et al. | |
| 2011/0081410 A1 | 4/2011 | Igarashi | |
| 2011/0143435 A1 | 6/2011 | Stayton et al. | |
| 2011/0287547 A1 | 11/2011 | Berkland | |
| 2012/0201872 A1 * | 8/2012 | Huang | A61K 9/1271 424/450 |
| 2013/0243699 A1 | 9/2013 | Wang et al. | |

FOREIGN PATENT DOCUMENTS

| AU | 2014215421 A1 | 8/2015 |
| CN | 1 757 398 A | 4/2006 |
| EP | 2 198 885 A1 | 6/2010 |
| EP | 2953646 A1 | 12/2015 |
| WO | WO 00/56288 A1 | 9/2000 |

(Continued)

OTHER PUBLICATIONS

Bisht et al., pDNA loaded calcium phosphate nanoparticles: highly efficient non-viral vector for gene delivery. International Journal of Pharmaceutics 288 (2005) 157-168.*
Kummitha et al., Albumin pre-coating enhances intracellular siRNA delivery of multifunctional amphiphile/siRNA nanoparticles. International Journal of Nanomedicine 2012:7 5205-5214 (Year: 2012).*
Longmuir et al., Effective targeting of liposomes to liver and hepatocytes in vivo by incorporation of a Plasmodium amino acid sequence. Pharm Res. Apr. 2006;23(4):759-69. (Year: 2006).*
Cao et al., Encapsulation of plasmid DNA in calcium phosphate nanoparticles: stem cell uptake and gene transfer efficiency. International Journal of Nanomedicine 2011:6 3335-3349 (Year: 2011).*
Bhakta et al., DNA encapsulated magnesium and manganous phosphate nanoparticles: potential non-viral vectors for gene delivery. Biomaterials 26 (2005) 2157-2163.

(Continued)

*Primary Examiner* — Christopher M Babic
*Assistant Examiner* — Arthur S Leonard
(74) *Attorney, Agent, or Firm* — Milstein Zhang & Wu LLC; Duan Wu, Esq.

(57) ABSTRACT

The present invention relates to the composition of a nanoparticle based on a magnesium salt, and methods of drug delivery using the nanoparticle. A preferred embodiment uses magnesium phosphate, with or without a shell to deliver aiRNA and/or siRNA. The nanoparticles of the present invention are also effective when administered orally.

25 Claims, 28 Drawing Sheets

Specification includes a Sequence Listing.

(56) References Cited

FOREIGN PATENT DOCUMENTS

| WO | WO2002034236 A2 | 5/2002 | |
|---|---|---|---|
| WO | WO 2008/131129 A1 | 10/2008 | |
| WO | WO 2009-029688 A2 | 3/2009 | |
| WO | WO 2011/017297 A2 * | 2/2011 | ............ A61K 48/00 |
| WO | WO 2013/040295 A2 | 3/2013 | |
| WO | WO2014057432 A2 | 4/2014 | |
| WO | WO-2014123935 A1 | 8/2014 | |

OTHER PUBLICATIONS

Bhakta et al., Magnesium Phosphate Nanoparticles can be Efficiently Used In Vitro and In Vivo as NonViral Vectors for Targeted Gene. Journal of Biomedical Nanotechnology (2008) vol. 4, 1-9.

Liu et al., An efficient calcium phosphate nanoparticle-based nonviral vector for gene delivery. International Journal of Nanomedicine (2011) 6, 721-727.

Gaglione et al., Recent Progress in Chemically Modified si RNAs. Mini Rev Med Chem, 2010, vol. 10, pp. 578-595. Especially p. 585, col. 1, para. 1; p. 588, col. 2, para. 2.

Li J. et al., Biodegradable calcium phosphate nanoparticle with lipid coating for systemic siRNA delivery. J Control Release, 2010, vol. 142, No. 3, pp. 416-421. Abstract, Section 2.3 The preparation of LCP, Fig. 1.

"Australian Application Serial No. 2014215421, Office Action dated Feb. 7, 2017", 5 pgs.

"Australian Application Serial No. 2014215421, Subsequent Examiners Report dated Feb. 5, 2018", 5 pgs.

"European Application Serial No. 14748796.1, Extended European Search Report dated Jan. 18, 2017", 13 pgs.

"European Application Serial No. 14748796.1, Partial Supplementary European Search Report dated Sep. 22, 2016", 7 pgs.

"European Application Serial No. 14748796.1, Response filed Apr. 12, 2016 to Communication pursuant to Rules 161(2) and 162 EPC dated Oct. 16, 2015", 18 pgs.

"European Application Serial No. 14748796.1, Response filed Jul. 28, 2017 to Extended European Search Report dated Jan. 18, 2017", 9 pgs.

"International Application Serial No. PCT/US2014/014751, International Preliminary Report on Patentability dated Aug. 20, 2015", 13 pgs.

"International Application Serial No. PCT/US2014/014751, International Search Report dated May 21, 2014", 4 pgs.

"International Application Serial No. PCT/US2014/014751, Written Opinion dated May 21, 2014", 11 pgs.

Breslow, R. et al. "Effects of metal ions, including Mg2+ and lanthanides, on the cleavage of ribonucleotides and RNA model compounds" Proc. Natl. Acad. Sci. USA, vol. 88, pp. 4080-4083, May 1991.

* cited by examiner

SPDP molecule

*In vitro* gene silencing: Yes (80-90%)
• aiRNA tested: survivin
• Cell Lines: SW480, DLD1
• aiRNA Concentrations: 100 – 400nM

*In vitro* gene silencing: SW480 (2' OMe aiRNA)

*In vivo* efficacy: SW480 xenograft

***In vivo* efficacy**: Yes (40%)
Day-15
• Tumor Xenograft: SW480
• aiRNAs tested: β-Catenin #0 & 2' OMe
• Dose: 1.5mg/kg

*In vitro* gene silencing: Yes (65-75%)
- aiRNA tested: β-Catenin
- Cell Lines: SW480
- aiRNA Concentrations: 75 – 150nM V13: 5x Calf-histone, 5% Cremaphor EL
V14: 5x Calf-histone, 4% Tween-80
V15: 5x Calf-histone, 4% Tween-20
V16: 5x Calf-histone, 3% Triton-X100
V17: 5x Calf-histone, 3x Cyclic RGD
V18: 5x Calf-histone, 3x Linear RGD x: times the amount of aiRNA

*In vitro* gene silencing: Yes (85-98%)
- aiRNA tested: *β-Catenin, PLK1, Survivin*
- Cell Lines: SW480
- aiRNA Concentrations: 35 – 100nM

| MgP based nanoparticle DDS- Surfactant Based | | Mean Size (nm) | Charge (mV) |
|---|---|---|---|
| K7 | MgP+ Protamine (5X) + Cremophore (5 %) | 13-21 | 15-18 |
| K7 C | MgP +Protamine (5 X) + Cremophore (5 %) + 3.5 % cyclodextrin | 13-20 | 14-16 |

| Control | | |
|---|---|---|
| bCat#0 chemgene | V13 | iv. Qd. Day1-4 3 nmole/m; day 5-8, day-9 6 nmole/animal, |
| bCat#0 chemgene | K7 | iv. Qd. Day1-4 3 nmole/m; day 5-8, day-9 6 nmole/animal, |

SEQUENCE LISTING

```
<160> NUMBER OF SEQ ID NOS: 8

<210> SEQ ID NO 1
<211> LENGTH: 15
<212> TYPE: RNA
<213> ORGANISM: Artificial sequence
<220> FEATURE:
<223> OTHER INFORMATION: part of an aiRNA pair targeting b-Catenin

<400> SEQUENCE: 1
cacaagaugg aauuu                                                      15

<210> SEQ ID NO 2
<211> LENGTH: 21
```

```
<212> TYPE: RNA
<213> ORGANISM: Artificial sequence
<220> FEATURE:
<223> OTHER INFORMATION: part of an aiRNA pair targeting b-Catenin

<400> SEQUENCE: 2
cuaguguucu accuuaaaua a                                              21

<210> SEQ ID NO 3
<211> LENGTH: 15
<212> TYPE: RNA
<213> ORGANISM: Artificial sequence
<220> FEATURE:
<223> OTHER INFORMATION: part of an aiRNA pair targeting survivin

<400> SEQUENCE: 3
gaucaacauu uucaa                                                     15

<210> SEQ ID NO 4
<211> LENGTH: 21
<212> TYPE: RNA
<213> ORGANISM: Artificial sequence
<220> FEATURE:
<223> OTHER INFORMATION: part of an aiRNA pair targeting survivin

<400> SEQUENCE: 4
ccucuaguug uaaaaguuua a                                              21

<210> SEQ ID NO 5
<211> LENGTH: 15
<212> TYPE: RNA
<213> ORGANISM: Artificial sequence
<220> FEATURE:
<223> OTHER INFORMATION: part of an aiRNA pair targeting PLK1

<400> SEQUENCE: 5
gaucacccuc cuuaa                                                     15

<210> SEQ ID NO 6
<211> LENGTH: 21
<212> TYPE: RNA
<213> ORGANISM: Artificial sequence
<220> FEATURE:
<223> OTHER INFORMATION: part of an aiRNA pair targeting PLK1

<400> SEQUENCE: 6
cuucuagugg gaggaauuua a                                              21

<210> SEQ ID NO 7
<211> LENGTH: 15
<212> TYPE: RNA
<213> ORGANISM: Artificial sequence
<220> FEATURE:
<223> OTHER INFORMATION: aiRNA sequence used as scramble control

<400> SEQUENCE: 7
guaguuauag ucgau                                                     15

<210> SEQ ID NO 8
<211> LENGTH: 21
<212> TYPE: RNA
```

```
<213> ORGANISM: Artificial sequence
<220> FEATURE:
<223> OTHER INFORMATION: aiRNA sequence used as scramble control

<400> SEQUENCE: 8
guccaucaau aucagcuaca a                                        21
```

BIODEGRADABLE AND CLINICALLY-COMPATIBLE NANOPARTICLES AS DRUG DELIVERY CARRIERS

CROSS-REFERENCE TO RELATED APPLICATIONS

This application claims priority to and the benefit of U.S. provisional patent application Ser. No. 61/761,012, filed Feb. 5, 2013, which application is incorporated herein by reference in its entirety to the extent allowed by applicable laws and regulations.

STATEMENT REGARDING FEDERALLY SPONSORED RESEARCH OR DEVELOPMENT

Not Applicable.

FIELD OF THE INVENTION

The present invention relates to novel nanoparticle compositions, method of making them and using them as drug delivery carriers.

BACKGROUND OF THE INVENTION

With the ever-expanding arsenal of therapeutic agents, including both macromolecule and small molecules, the biomedical and pharmaceutical industries had increasingly realized the importance of a safe, practical and effective delivery vehicle of these therapeutic agents for the mammalian especially the human population. There are many desired characteristics for a satisfactory delivery vehicle: it needs to be nontoxic, therefore, biocompatible, preferably biodegradable or absorbable within a reasonable time period. For systemic administration, it needs to be stable enough to circulate to the target site while shielding the therapeutics from being degraded or digested in the body, and avoid significant immune responses unless the delivery is actually designed to trigger such responses. It needs to be able to penetrate physiological barriers in order to access target tissues, cells, cellular compartments or organelles. It also needs to be soluble enough under the physiological conditions of a target site or during a target time period to release the agents it carries. Furthermore, a controlled release of the therapeutic agents over time often is highly desired.

Among new kinds of therapeutic agents developed in recent decades are those based on the natural process of RNA interference (RNAi) after its discovery in 1998 by Fire and Mello in *C. elegans*. Central to the process of RNAi are two types of ribonucleic acid (RNA) molecules: microRNA (miRNA) and small or short interfering RNA (siRNA). Researchers have been developing promising therapeutic applications based on both types of molecules and their roles in both plants and animals, most notably in transcriptional and post-transcriptional gene silencing. For example, exogenous siRNAs or their expression vectors have been engineered to be introduced directly to a host or expressed in host cells to regulate gene expression implicated in development, immune response and diseases.

A new kind of RNA molecules based on the naturally occurring siRNA form (double-stranded and 21 base pairs long with 2-nucleotide 3' overhangs on both strands) has also been rationally devised. It is called asymmetrical interfering RNA (aiRNA). See, PCT Patent Publication WO 2009/029688. Advantages of aiRNA over siRNA include better efficacy and potency, rapid onset of action, better durability, a shorter length of the RNA duplex to avoid non-specific interferon like response, reduced off-target effects, and reduced cost of synthesis.

Despite the explosion of immense interest in RNAi, and with many calling it the most important pharmacological advance in recent history, researchers have come to realize that the success of RNAi-based therapy in mammals depends, in large parts, on the intracellular delivery of siRNAs to specific tissues and organs where the gene of interest is expressed. See Vaishnaw, A. et al., "A status report on RNAi therapeutics," *Silence* (2010) 1:14. In fact, the lack of a satisfactory delivery system has increasingly become the bottleneck in harnessing the power of RNAi therapeutics as many other aspects of technical hurdles are being resolved. See Davidson, B. et al., "Current prospects for RNA interference-based therapies," *Nature Reviews* (May 2011) 12:329-340. For example, one challenge in devising a reliable delivery system for siRNA is to increase the circulation half-life of siRNA in blood and to avoid premature renal excretion. To that end, researchers have modified the siRNAs using a conjugation-based approach to some success. For instance, in a mouse system, cholesterol-conjugated siRNAs administered intravenously have been shown to significantly increase in the circulation half-life and knockdown of the target mRNA in the liver. See Soutschek J., et al. *Nature* (2004) 432: 173-178. However, the biggest challenge remains to be designing a delivery system that can be clinically compatible as well as capable of delivering sufficient silencing RNA to tissues and cells to achieve meaningful gene silencing.

The search for an optimal drug delivery system has also lead researchers to nanoparticle technologies, which have shown great potential in both spatial and temporal controls in drug delivery. Many nanoparticles have been proposed for use as carriers for biological macromolecules such as proteins and nucleic acids, see, e.g., U.S. Pat. Nos. 5,219,577 and 7,651,694. In 2010, reports surfaced of effective systemic administration of siRNA to patients via a targeted delivery system in which nanoparticles made of a cyclodextrin-based polymer is used, see Davis, M. et al. *Nature* (2010) 464, 1067-1070. However, the cyclodextrin-based nanoparticle approach, while promising, only showed marginal gene silencing efficacy after systemic administration. Novel nanoparticle technology is still urgently needed to achieve necessary delivery efficiency for drug efficacy.

Most of the current exploration of nano-scale delivery vehicles for RNAi-based therapeutic agents has focused on liposome-based carriers or polymer-based carriers. Nanoparticles based on other constitutions such as metals (e.g., gold) and calcium phosphate (see Li, J. et al. *J Control Release*. (2010) 142(3): 416-421) have also been studied but to a much lesser extent. However, there are ongoing concerns and disappointment over the lack of biodegradability with certain metals and their ensuing cytotoxicity, and over the safety and delivery efficiency of calcium-phosphate particles. As a result, despite their potential advantages over viral vectors, the applicability of nanoparticles made of these materials continues to be limited as viable delivery tools of biologically active molecules. Accordingly, there remains a great need for innovative nonviral nanoparticle compositions as drug delivery vehicles.

SUMMARY

The present invention provides new materials and compositions of nanoparticles that can be used for delivering therapeutic agents including those based on RNAi technologies.

In one aspect, the present invention provides a nanoparticle for delivering a medically useful agent or a therapeutic agent where the nanoparticle includes a biodegradable and clinically compatible core including a magnesium salt and a medically useful agent. In some embodiments, the core consists of a carrier or inactive ingredient that consists substantially of a magnesium salt only—in other words, in those embodiments, there is substantially no other inactive ingredient used to constitute the core. The magnesium salt can be inorganic, such as magnesium phosphate, or organic. The medically useful agent, or the active therapeutic ingredient, for example, can be a nucleic acid, a protein or peptide, or a small molecule. The nucleic acid may be selected from the group consisting of an antisense DNA, an RNA, a DNA-RNA hybrid, a PNA, and an aptamer. In an embodiment, the RNA includes aiRNA. In another embodiment, the RNA includes siRNA, or a mixture of siRNA and aiRNA. In one feature, the aiRNA or siRNA targets at least a messenger RNA (mRNA) that either encodes a protein or regulates a part of a biological pathway implicated in a mammalian disease. In an alternate embodiment, the protein or peptide is an antibody or an antibody fragment.

In one feature, the medically useful agent is disposed inside the core of the nanoparticle. In an alternate feature, the medically useful agent is disposed on a surface of the core of the nanoparticle.

Optionally, in one feature, the core of the nanoparticle of the invention may also include calcium phosphate. Further, the core may also include an additive such as a nucleic acid, a protein or small peptide, a lipid, a surfactant, an amino acid, a carbohydrate, a small molecule, and/or a biocompatible polymer.

In one feature, the nanoparticle of the invention further includes a shell or coating around the core; the shell may comprise a surfactant (e.g., CREMOPHOR® EL, TWEEN®-20, TWEEN®-80, SOLUTOL®, and/or TRITON®), a protein or small peptide (e.g., histone and/or protamine), a lipid, a ligand, an amino acid, a carbohydrate, a nucleic acid, a small molecule and/or a biocompatible polymer. In some embodiments, the core or the shell, may contain a targeting ligand, including cell-type-specific, tissue-specific targeting ligand and homing ligand, a cell-penetrating peptide (e.g., polyarginine and polylysine), an albumin, an albumin derivative, a histone, a protamine, CREMOPHOR® EL, SOLUTOL®, TWEEN®, TRITON®, cyclodextrin, RGD tripeptide, cholesterol, a phospholipid, polyethylene glycol (PEG), or a combination thereof.

In some embodiments, the average diameter of the nanoparticle of the invention (including any shell) is about 200 nanometers or less, or, preferably, between about 5 nanometers and about 100 nanometers, more preferably, between about 5.5 nanometers and about 80 nanometers, and even more preferably, between about 5.5 nanometers and about 30 nanometers.

In one feature, the nanoparticle of the invention is more soluble in a solution with a pH value between about 6.0 and about 7.0 than in one with a pH of about or above 7.0. In one embodiment, the nanoparticle is even more soluble in a solution with an acidic pH equal to or less than about 6.0 than in one with a pH of about 7.0.

In another feature, the nanoparticle of the invention is characterized with a surface charge (on a coating or shell, if any) between about −30 mV and about +50 mV, or preferably, between about −10 mV and about +20 mV, or even more preferably, between about −5 mV and about +10 mV.

These and other features of the invention apply to all embodiments described herein unless explicitly disclaimed.

In a first embodiment, the present invention provides a nanoparticle that includes a core substantially consisting of a magnesium salt, and a medically useful agent coated on a surface of the core. The magnesium salt is preferably magnesium phosphate. The nanoparticle may optionally include a shell around the core. And the medically useful agent may be aiRNA, siRNA or a mixture thereof.

In a second embodiment, the present invention provides a nanoparticle that includes a core that, in turn, includes only a magnesium phosphate and one or more medically useful agents disposed inside said core. The nanoparticle may optionally include a shell around the core. And the medically useful agent may be aiRNA, siRNA or a mixture thereof.

In a third embodiment, the present invention provides a nanoparticle that includes a core that, in turn, includes only magnesium phosphate, calcium phosphate, and one or more medically useful agents. The nanoparticle may optionally include a shell around the core. And the medically useful agent may be aiRNA, siRNA or a mixture thereof. And the medically useful agent may be aiRNA, siRNA or a mixture thereof.

In a fourth embodiment, the present invention provides a nanoparticle that includes a core that, in turn, includes magnesium phosphate, a biocompatible additive, and a medically useful agent. The additive may be a lipid, a surfactant, a protein or peptide, albumin or albumin derivatives, a nucleic acid, a carbohydrate, an amino acid, a biocompatible polymer, polyarginine, polylysine, or a polyalkylene glycol (e.g. PEG). The lipid may be cholesterol or a phospholipid. And the medically useful agent may be aiRNA, siRNA or a mixture thereof. There may be an optional shell surrounding the core. The shell may include various ingredients as described above in summary and below in detail.

In a preferred embodiment, the present invention provides a nanoparticle that includes a core that, in turn, includes magnesium phosphate with aiRNA disposed inside said core, a shell around the core and including a surfactant (e.g., CREMOPHOR® EL, SOLUTOL®, TWEEN® or TRITON®), a protein or peptide (e.g., histone and/or protamine), a lipid, a ligand, an amino acid, a carbohydrate, a small molecule, a nucleic acid, and/or a biocompatible polymer. And the average diameter of the nanoparticle is between about 2 nanometers and about 200 nanometers, more preferably between about 5 nm and about 100 nm, 80 nm or 50 nm. The protein or peptide may be an albumin or an albumin derivative, and the lipid may be cholesterol or a phospholipid. In a particularly preferred embodiment, a nanoparticle of the invention includes a magnesium phosphate core mixed or loaded with an active agent; the core is further surrounded by a shell that includes one or more surfactants. In a method embodiment of the invention, a nanoparticle is manufactured by coating its core with a surfactant to achieve a size of between about 5 nm and about 50 nm.

In another aspect of the invention, a pharmaceutical composition is provided including the nanoparticles of the invention, e.g., a plurality of nanoparticle that each includes a biodegradable and clinically compatible core including a magnesium salt and a medically useful agent. In an embodiment, the composition further includes a pharmaceutically acceptable excipient, carrier or diluent. In a preferred embodiment, the pharmaceutical composition of the present invention is formulated for oral administration.

In a further aspect of the invention, a method is provided that treats a disease or condition in a mammalian subject. The method includes administering to the mammalian subject a therapeutically effective amount of a pharmaceutical composition of the invention. In a preferred embodiment, the composition is administered orally into the subject.

In yet another aspect of the invention, a method is provided for delivering an active agent into a mammalian subject. The method includes administering to the mammalian subject a plurality of nanoparticles, each being a nanoparticle of the invention. In a preferred embodiment, the nanoparticles are administered orally into the subject.

In an embodiment of the invention, a method of delivering an active agent into a mammalian subject is provided. The method includes administering orally into the subject at least one nanoparticle loaded with an active agent, and preferably a plurality of nanoparticles each loaded with said agent. The active agent may be an active pharmaceutical ingredient. In a particular embodiment, the nanoparticle comprises a core that includes a magnesium salt and the active agent is either an aiRNA or siRNA. In an embodiment, a method is provided for treating a disease in a mammalian subject, said method comprising administering orally into said mammalian subject a therapeutically effective amount of an active pharmaceutical ingredient carried by a plurality of nanoparticles, preferably with cores comprising a magnesium salt.

Related to these aspects, the present invention provides nanoparticles and pharmaceutical compositions that are effective in orally delivering an active agent, e.g., a pharmaceutical ingredient or a medically useful agent into a mammalian subject. In a preferred embodiment, a pharmaceutical composition is provided with a nanoparticle and an active pharmaceutical ingredient, where the composition is capable of, after being administered orally, eliciting medicinal or therapeutic effects treating at least one disease or condition such that the composition would qualify as a pharmaceutical candidate meeting normal requirements for clinical applications, alone or in combination with other pharmaceuticals.

A further aspect of the invention provides a nanoparticle that includes an albumin-based core and a medically useful agent. The core may include a peptide that is a modified albumin, an albumin fragment or a derivative of albumin. The nanoparticle may further include a magnesium slat such as magnesium phosphate. As in other embodiments of the invention, the medically useful agent may be an antisense DNA, an RNA, a DNA-RNA hybrid, a PNA, aptamer, an antibody, an antibody fragment and a small molecule.

According to yet another aspect of the invention, a nanoparticle is provided with a core that includes gold and an aiRNA. In an embodiment, aiRNA is coated on the surface of a substantially gold core. The core may further include magnesium phosphate, preferably coated on the core in the same layer with aiRNA as a mixture or in a separate layer. The nanoparticle may further include an optional shell around the core. The shell may include a protein or peptide, a lipid, a surfactant, a ligand, an amino acid, a carbohydrate, a small molecule, a nucleic acid, or a biocompatible polymer. The aiRNA, in one feature, targets at least an RNA that either encodes a protein or regulates a part of a biological pathway implicated in autoimmune disease, or an inflammatory disease. In one embodiment, the aiRNA targets human TNF-α (tumor necrosis factor-α) function. In another embodiment, the aiRNA targets human IL-6 (Interleukin-6) function.

Other aspects and embodiments of the present invention are set forth or will be readily apparent from the following detailed description of the invention.

DETAILED DESCRIPTION

Figure 1:
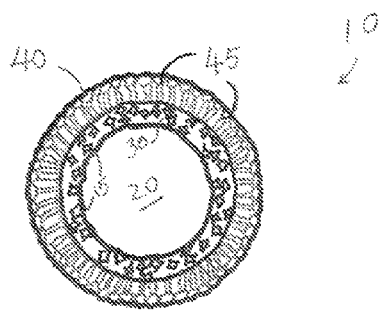
FIGS. 1-4 illustrate various embodiments of the nanoparticle of the invention in cross-sectional views.

All references cited herein are incorporated herein by reference in their entirety to the extent allowed by applicable laws and for all purposes to the same extent as if each individual publication or patent or patent application is specifically and individually indicated to be incorporated by reference in its entirety for all purposes. To the extent publications and patents or patent applications incorporated by reference contradict the disclosure including definitions contained in the present specification, the specification is intended to supersede and/or take precedence over any such contradictory material.

Unless defined otherwise, all technical and scientific terms used herein have the same meaning as is commonly understood by one of ordinary skill in the art to which this invention belongs.

As used herein, the singular form "an", and "the" include plural references unless the context clearly dictate otherwise. For example, the term "a cell" includes a plurality of cells including mixtures thereof.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "clinically compatible" refers to the characteristic of a composition or formula that can be prepared and readily administered to patients with sufficient safety above applicable regulatory requirements.

As used herein, "encapsulated", "embedded" "entrapped" or "incorporated" and their derivative terms refer to being complexed, encased, bonded with, coated with, layered with or enclosed by a substance. Thus, a substance or agent encapsulated in a particle means the substance or agent is incorporated into the particle structure, or coated/attached to the particle surface, or both.

The terms "isolated" or "purified" as used herein refer to a material that is substantially or essentially free from components that normally accompany it in its native state.

Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Terms such as "treating" or "treatment" or "to treat" or "alleviating" or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented.

Magnesium plays important roles in many cellular functions in mammalians. It is the fourth most abundant mineral in the human body. It is needed for more than 300 biochemical reactions in the body and helps maintain strong bones, normal muscle and nerve functions, and a regular heart rhythm. It also participates in carbohydrate metabolism and protein synthesis. And its deficiency may result in many symptoms and diseases, e.g., hyperexcitability, dizziness, muscle cramps, muscle weakness, fatigue, and diabetes.

The human body normally absorbs magnesium through dietary intake and about 50% of total body magnesium is used to build bones. The vast majority of the other half is found in cells of body tissues and organs with about 1% in blood. According to the Food and Nutrition Board at the Institute of Medicine, part of National Academies, the Recommend Dietary Allowances (RDA) for an adult male is at or above 400 mg/day, and for an adult non-pregnant female is at or above 310 mg/day. Close to 60% of the U.S. population do not meet the U.S. RDA for dietary intake of magnesium, according to a 2009 study by the Community Nutrition Mapping Project. Therefore, magnesium and many magnesium ions are not only safe, biocompatible and absorbable by the human body, but also provide much needed nutrition.

Magnesium salts produce divalent cations $Mg^{2+}$, and as inorganic particles, are not subjected to microbial attacks and have good storage stability. They can form complexes with macromolecules as well as small molecules and transport across cell membrane via ion channel mediated endocytosis.

Accordingly, the present invention provides:

A. NANOPARTICLES BASED ON MAGNESIUM-SALT AND ENCAPSULATED WITH MEDICALLY USEFUL AGENT

In a basic form, the invention can be characterized as providing a nanoparticle that includes a biodegradable and clinically compatible core comprising a magnesium salt, where the nanoparticle encapsulates a medically useful agent.

The core is generally and substantially spherical in shape, meaning it is substantially round or oval in cross-sections and includes particles that do not have faceted and are substantially smooth or that have facets. The core may be faceted or angular and still falls within what is contemplated by the present invention.

The magnesium salt useful in the present invention are preferably inorganic magnesium salt, e.g., magnesium phosphate, but can be organic in some embodiments as well, e.g., magnesium organophosphate. Magnesium phosphate (sometimes abbreviated as "MgP" herein) can mean magnesium phosphate tribasic $Mg_3(PO_4)_2$, magnesium phosphate dibasic or dimagnesium phosphate $MgHPO_4$, or monomagnesium phosphate $Mg(H_2PO_4)_2$, or a combination of any of the above. Magnesium phosphate dissolves better in acidic conditions. Compared to an aqueous environment where the pH is about 7.0, solubility of magnesium phosphate increases in a solution where the pH value is between 6.0 and 7.0, even further when pH is below 6.0, and even further more when pH is below 5.0. And other one or more magnesium salts that exhibit similar solubility increases in an acidic condition can be also used, either instead of or in addition to, the magnesium phosphate for purpose of the present invention.

The medically useful agent encapsulated in the nanoparticle of the invention, for delivery to a target site, can be a biologically active macromolecule or a small molecule. It can be a therapeutic, a drug or a diagnostic agent. Examples of diagnostic agents include imaging contrast agents that enable the visualization of the site of drug delivery.

Generally speaking, the medically useful agent useful in the present invention can be a nucleic acid, a protein or peptide, a polysaccharide, a carbohydrate, a lipid, a small molecule or a combination of any of the above. The agent could be one or more macromolecules that have been conjugated or otherwise chemically modified to change their solubility, charge profile, stability, size, shape, and so on. The nucleic acid may be a DNA (e.g., an antisense DNA), an RNA, a DNA-RNA hybrid, a PNA, and an aptamer. In an embodiment, the RNA includes aiRNA. In another embodiment, the RNA includes siRNA. In one embodiment, the nanoparticle of the invention encapsulates a mixture of aiRNA and siRNA. In one feature, the aiRNA and/or siRNA targets at least an RNA that either encodes a protein or regulates a part of a biological pathway implicated in a mammalian disease. In an alternate embodiment, the protein or peptide is an antibody or an antibody fragment.

Many drugs can be readily incorporated into the nanoparticles of the invention. Examples of these include and are not limited to: insulin, a growth hormone, a steroid, an interferon, an anti-cancer drug, an antibiotic, an anti-viral drug, a therapeutic antibody, an anti-clotting agent such as heparin, and so on. As used herein, the terms "cancer" and "cancerous" refer to or describe the physiological condition in mammals in which a population of cells are characterized by unregulated cell growth.

In an embodiment, the medically useful agent useful in the present invention is an energy conductor suitable for hyperthermia or hypothermia therapies including laser ablation or the like.

The medically useful agent can be inside the core, on the surface of the core, or both. The core can be solid with a substantially smooth surface, or porous with a surface dotted with openings. The core can be coated or naked. When the surface of the core is coated with a material, that material forms a coating that is termed a "shell" in this specification. The shell can be porous and does not have to surround or enclose the entire core surface, although it certainly does in some embodiments. There may be multiple layers of shells around a core.

In addition to the magnesium salt, the core can further include calcium phosphate, another bioabsorbable material that has been used as the core material for nanostructures. See Khosravi-Darani, K. et al. *Acta Medica Iranica* (2010) 48(3): 133-141.

When the additives are coated or adsorbed onto the core surface, a shell forms around the core. Besides helping reduce or maintain the nanoparticle size, preserving or modulating the charge of the nanoparticle as described above, components of the optional shell may also serve other important purposes. In general, the shell protects the core and its payload from lysosome, enzymatic, as well as DNase or RNase degradation, prolongs its circulation in the blood, and helps achieve time-controlled release of the payload. See, e.g., Li, J. et al. *J Control Release* (2010) 142(3): 416-421. The addition of some, preferably biodegradable, polymers, e.g., PEG or a nucleic acid, helps keep the particle size small and obtains good colloidal stability through their steric effect. The PEG may have a molecular weight from about 500 daltons to about 20,000 daltons, e.g., about 500, 1000, 5000, 10,000, 15,000, and 20,000 daltons.

In one feature of the present invention, one or more surfactants are coated or adsorbed onto the surface of the nanoparticle core. Surprisingly, surfactants contributed greatly in achieving the goal of reducing and maintaining the size of the nanoparticles. For delivering a medically usefully agent in a biophysical environment, the average size of the nanoparticles is preferably between about 5 nm and about 200 nm, and more preferably between about 5 nm and about 100, 80, or even 60 nm in order to be able to pass through certain biological barriers yet without being filtered out immediately from the blood stream. In some embodiments of the present invention, surfactant additives have reduced particle sizes not only to the ranges recited above but further down to the range between about 5 nm and about 50 nm, or even further to less than about 20 nm or 15 nm, a great technical challenge to all makers of nanoparticles. In various embodiments of the present invention, the surfactant additive is nonionic, for example, an alcohol such as a fatty alcohol, stearyl alcohol, cetyl alcohol, cetostearyl alcohol and oleyl alcohol. In a preferred embodiment, the surfactant is CREMOPHOR® EL® (generally referred herein as "CREMOPHOR®"), TWEEN®-20 or -80 (also known as polysorbate-20 or -80, generally referred herein as "TWEEN®" sometimes), SOLUTOL® HS 15, and/or TRITON®.

Other potential additives that can be part of the shell of the nanoparticle of the present invention include: aiRNA and/or siRNA, protein or peptide (e.g., albumin or its derivative, and preferably, protamine and/or histone), lipid (e.g., cholesterol, or phospholipids), carbohydrate, excipient, and a targeting ligand such as a cell-type-specific, tissue-specific targeting ligand or homing ligand (e.g., a ligand for a cell surface marker, an antibody or an antibody fragment, nanobody). Such ligand helps direct the nanoparticle to specific target tissue or cell (e.g., cancer cells). In one embodiment, the targeting ligand is anisamide, a sigma-1 receptor ligand, which can be combined with a PEG, and tethered to the nanoparticle of the invention to target tumor cells. See Guo J. et al. *Biomaterials* (2012) 33(31): 7775-7784.

Another optional additive to a nanoparticle of present invention is a cell-penetrating peptide that helps facilitate cellular intake of the nanoparticle. A typical cell-penetrating peptide contains an amino acid sequence that either contains relative abundance of positively charged amino acids (polycatonic), e.g., polyarginine and polylysine, or an alternating pattern of polar/charged amino acids and non-polar, hydrophobic amino acids (amphipathic), or a derivative or mimetic of a naturally occurring cell penetrating peptide, such as HIV Tat.

Accordingly, referring to FIG. 1, in an illustrative embodiment of the invention, a nanoparticle 10 includes a substantially spherical core 20. The core 20 substantially consists of only a magnesium salt, e.g., magnesium phosphate. In one embodiment, it consists of substantially pure magnesium phosphate only. The surface of the core 20 is coated with a layer 30 of the medically useful agent 15 (e.g., aiRNA and/or siRNA), forming a first shell around the core 20. The adsorption of the medically useful agent 15 may help stop nanoparticle growth or aggregation, thereby keeping its size small.

Optionally, a second layer 40 of one or more additives forms an outer shell surrounding the first shell 30. The exemplary additive illustrated here is a lipid 45, but can be any of the additives described in this specification, e.g. a surfactant.

Figure 2:
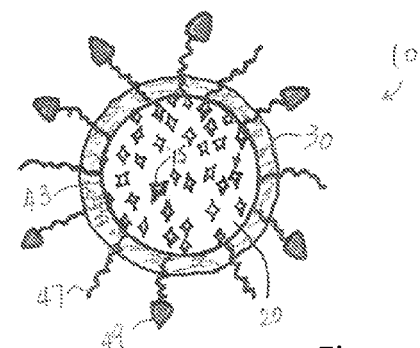

Referring to FIG. 2, in another illustrative embodiment of the invention, a nanoparticle 10 includes a core 20 where the medically useful agent 15 (e.g., aiRNA and/or siRNA) is encapsulated inside a magnesium salt (e.g., magnesium phosphate). An optional shell 30 around the core 20 includes one or more additives. The exemplary additives illustrated in the figure here include albumin 43, PEG 47 and PEG with a targeting ligand 49, but can be any of the additives described in this specification, e.g., one or more lipids, biodegradable polymers, surfactants, proteins and excipients.

Figure 3:
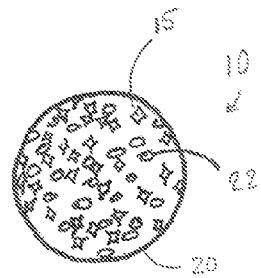

Referring now to FIG. 3, in another illustrative embodiment of the invention, a nanoparticle 10 includes a core 20 where the medically useful agent 15 (e.g., aiRNA and/or siRNA) is encapsulated inside a mixture of a magnesium salt (e.g., magnesium phosphate) and calcium phosphate 22. In the illustrated version, the core 20 is naked, but can have one or more optional shells around it. Calcium phosphate (sometimes abbreviated as "CaP" herein) can mean $Ca_3(PO_4)_2$, $CaHPO_4$, or $Ca(H_2PO_4)_2$, or a combination of any of the above.

Figure 4:
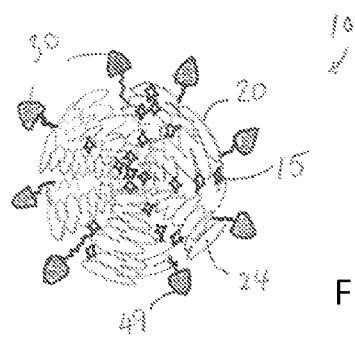

Referring now to FIG. 4, in yet another illustrative embodiment of the invention, a nanoparticle 10 includes a core 20 where the medically useful agent 15 (e.g., aiRNA and/or siRNA) is encapsulated inside a mixture of a magnesium salt (e.g., magnesium phosphate) and a biocompatible polymer 24. In the illustrated version, the core 20 is surround by an optional shell 30 formed by an exemplary targeting ligand 49. The shell 30, in this exemplary version, is rather porous; such is also the case for the core 20.

The invention also provides a pharmaceutical composition comprising the nanoparticles described herein and a pharmaceutically acceptable excipient, carrier, or diluent. Suitable carriers and their formulations are known in the art and are described in Remington, *The Science and Practice of Pharmacy*, 20th Ed. Mack Publishing (2000). The pharmaceutical composition may be formulated in the form of liquid, capsule, tablet, powder, and aerosol; and may be formulated in the form suitable for intravenous, intramuscular, intradermal, oral delivery, mucosal delivery, topical, or delivery to an ocular surface, etc. The composition may include other components, such as buffers, preservatives, nonionic surfactants, solubilizing agents, stabilizing agents, emollients, lubricants and tonicity agents. The composition may be formulated to achieve controlled release for the macromolecules.

Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions of the present invention.

B. METHODS OF MAKING THE NANOPARTICLES OF THE INVENTION

Magnesium salt-based nanoparticles can be prepared through either a double emulsion process or nano-precipitation process, or adapted from other well-known processes for making nanoparticles.

Figure 5:
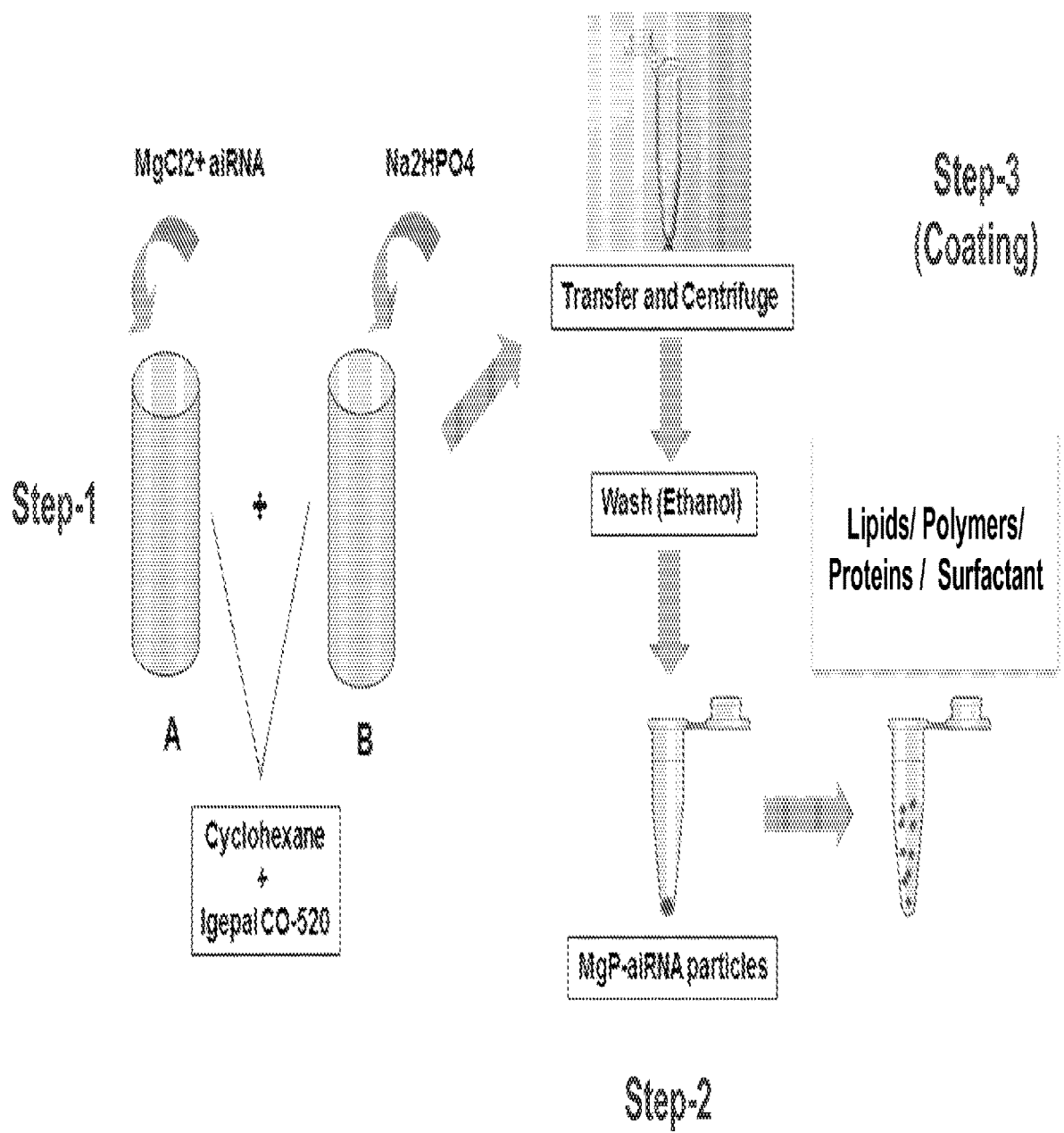
FIG. 5 schematically illustrates exemplary methods for making the nanoparticles of the present invention where their magnesium-based cores loaded with aiRNA are further coated with a shell that, in various embodiments, may contain lipids, polymers, proteins and/or surfactants.

Exemplary Method I:

Referring to FIG. 5, in Step-1, a first emulsion is prepared by first mixing desired amount of a medically useful agent, e.g., aiRNA solution, and a magnesium salt aqueous solution (e.g., $MgCl_2$, or magnesium nitrate), and then adding the aqueous solution to an organic solution with or without a surfactant (e.g., Cyclohexane/Igepal CO-520 (71/29, v/v) under vigorous stirring to form a well dispersed micro-nano-emulsion. To make a calcium-based core, or to add calcium to the core, either replace $MgCl_2$ with $CaCl_2$) or simply add $CaCl_2$. The mixture is further incubated at room temperature. The organic solution mixture can be prepared by mixing cyclohexane/Igepal CO-520 solution (71/29 v/v) with continuous spinning on a magnetic stirrer to ensure mixing.

A second emulsion is prepared by adding a phosphate salt (e.g. disodium hydrogen phosphate ($Na_2HPO_4$,) or, diammonium hydrogen phosphate) aqueous solution under vigorous stirring to an organic solution with or without a surfactant (e.g., Cyclohexane/Igepal Co-520 (71/29, v/v) to form a well-dispersed micro- or nano-emulsion. The mixture is further incubated at room temperature.

The second emulsion is then added very slowly, e.g. drop-by-drop, into the first emulsion under vigorous stirring, forming a combination mixture. The ratio between the first emulsion and the second emulsion in the combination mixture is critical for achieving desirable particle size, and in various embodiments, is about 10-20 versus 1. The combination mixture is further incubated at room temperature for a certain time depending on their desired sizes.

Then, in Step-2, a solvent (e.g., absolute ethanol) is added to wash the nanoparticles yielded from the above step. Supernatant is removed through a centrifuging process. The yielded nanoparticles, each with a core consisting of substantially only an inorganic magnesium salt (MgP), are dried under low-pressure conditions or simply air-dried.

In the coating step (Step-3 as illustrated), a shell is formed around the nanoparticles after they are suspended and combined with selected ingredients for the shell such as lipids, biodegradable polymers, proteins and/or surfactant. For example, to make a protein/surfactant-based shell around the nanoparticle of the invention, a solution of proteins with or without surfactants (e.g., 1× (w/w in relation to the load) histone and 1% surfactant (v/v)) is first prepared in nuclease-free water (or, saline, human albumin solution (e.g. 10%)) and incubated at room temperature. The solution is added to dry tubes of the MgP cores loaded with aiRNA, and then mixed completely. The mixture is then sonicated, e.g., using a water bath sonicator, to achieve a nano-suspension to prevent aggregation. The suspension is, optionally, pH-adjusted to 7.0, incubated at room temperature, and centrifuged for its supernatant to be collected, analyzed and used for therapeutic administration. The nanoparticle preparation can also be formulated per administration route or purpose, as is well known in the art.

Nanoparticles with shells that are lipid-based or polymer-based can be prepared in similar fashions. For example, to make a lipid-based shell, the desired lipid content can be mixed in appropriate ratios and made into a dry film by using a rotavap for 3-4 hours. The necessary volume of phosphate buffer saline is then added to reconstitute the dry film. After the desired volume of the solution is added to dry tubes of the MgP cores loaded with aiRNA and mixed completely, follow the same sonication step for 5 minutes at room temperature and the centrifugation step for 30 seconds.

Exemplary Method II:

In an alternative embodiment, the medically useful agent, e.g., aiRNA, is added to magnesium salt-based nanoparticles after the nanoparticles are first formed as described above except without the medically useful agent in the first emulsion. One or more selected materials (e.g., albumin or its derivatives, surfactant, cyclodextrin or amino acids) for the shell are also added similar to ways described above to the nanoparticles.

C. METHODS OF USING THE NANOPARTICLES OF THE INVENTION

The present invention also provides a method of treating a disease in a mammalian subject. The method includes administering to the mammalian subject a therapeutically effective amount of a pharmaceutical composition of the invention.

The invention also provides a method for delivering an active and medically useful or medical agent into a mammalian subject. The method includes administering to the mammalian subject a plurality of nanoparticles, each being a nanoparticle of the invention. Besides therapeutics, the active agent can also be an imaging agent such as one useful for radiopharmaceutical imaging.

Administration of the composition of the invention may be by any means known in the art, including: orally, intravenously, subcutaneously, via inhalation, intraarterially, intramuscularly, intracardially, intraventricularly, parenteral, intrathecally, and intraperitoneally. Administration may be systemic, e.g. intravenously, or localized.

In some embodiments, the nanoparticles of the pharmaceutical composition include an enteric coating. Enterically coated particles may be suitably administered by oral route.

The particles of the invention may be used to deliver the medically useful agents to a mucosal surface for mucosal immune protection, mucosal vaccine delivery, or mucosal drug delivery. Specifically, therapeutic agents may be delivered via the nanoparticles of the invention to mucosal surface in the respiratory tracts to treat a respiratory disease, the ocular surface to treat an ocular disease, the gastrointestinal tracts to treat a gastrointestinal disease. In an embodiment, agents are delivered via the nanoparticles of the invention topically to treat dermatological indications. Non-limiting examples of medically useful agents include one or more of the following: antigenic material, natural immunoenhancing factors, polynucleotide material encoding immunogenic polypeptides, therapeutic drugs, such as insulin, anti-cancer drugs, or any other composition capable of having a therapeutic effect when administered to a mucosal surface. The particles may be complexed with any physiological acceptable excipient and administered through mucosal surfaces, such as orally, intrapulmonary, nasally, rectally, or ocularly.

In a preferred embodiment, nanoparticles of the present invention are administered orally to a mammalian subject to deliver an active agent and/or to treat a condition or disease. Oral deliver using nanoparticles face particular challenges as whatever formulation of the particles need to not only protect the active agent from strong enzymatic digestion in the digestive system but also get the agent absorbed into the circulatory system. Various formulations of the nanoparticles of the present invention have been proven to have therapeutic efficacy, e.g., substantial gene silencing effect, when administered orally to a mammalian subject.

In an embodiment, the pharmaceutical composition of the invention is used to treat oncological indications as well as diseases associated with the pathology of liver and hepatocytes. In another embodiment, the pharmaceutical composition of the invention is used to treat metabolic diseases, e.g., those associated with the liver.

In another embodiment, the pharmaceutical composition of the invention is used to treat colon cancer and other oncological indications.

D. EXAMPLES

Example 1: GFP Transfection Using Nanoparticles with Magnesium Phosphate Cores Nanoparticles were prepared using the double-emulsion process described above. Specifically, 100 µL of 500 mM $MgCl_2$ was mixed with plasmid DNA coded for the green fluorescence protein (GFP) before being added to 5 mL of Cyclohexane/Igepal CO-520 (71/29, v/v) under vigorous stirring. The second emulsion was prepared from 100 µL of 25 mM $Na_2HPO_4$. And after the resulting MgP cores loaded with DNA were dried, a nuclease-free aqueous solution with 10× (w/w in relation to the plasmid DNA) histone and 1% surfactant (v/v) was added to them. The resulting mixture produced nanoparticles with a clinically compatible core consisting of a magnesium salt as carrier for the agent, in this case, GFP-coding DNA, where the core is further surrounded by a shell or coating that has both a surfactant and a small peptide (histone). The carrier material of the core consisted of only a substantially pure magnesium salt and no other material in this particular example.

Figure 6:
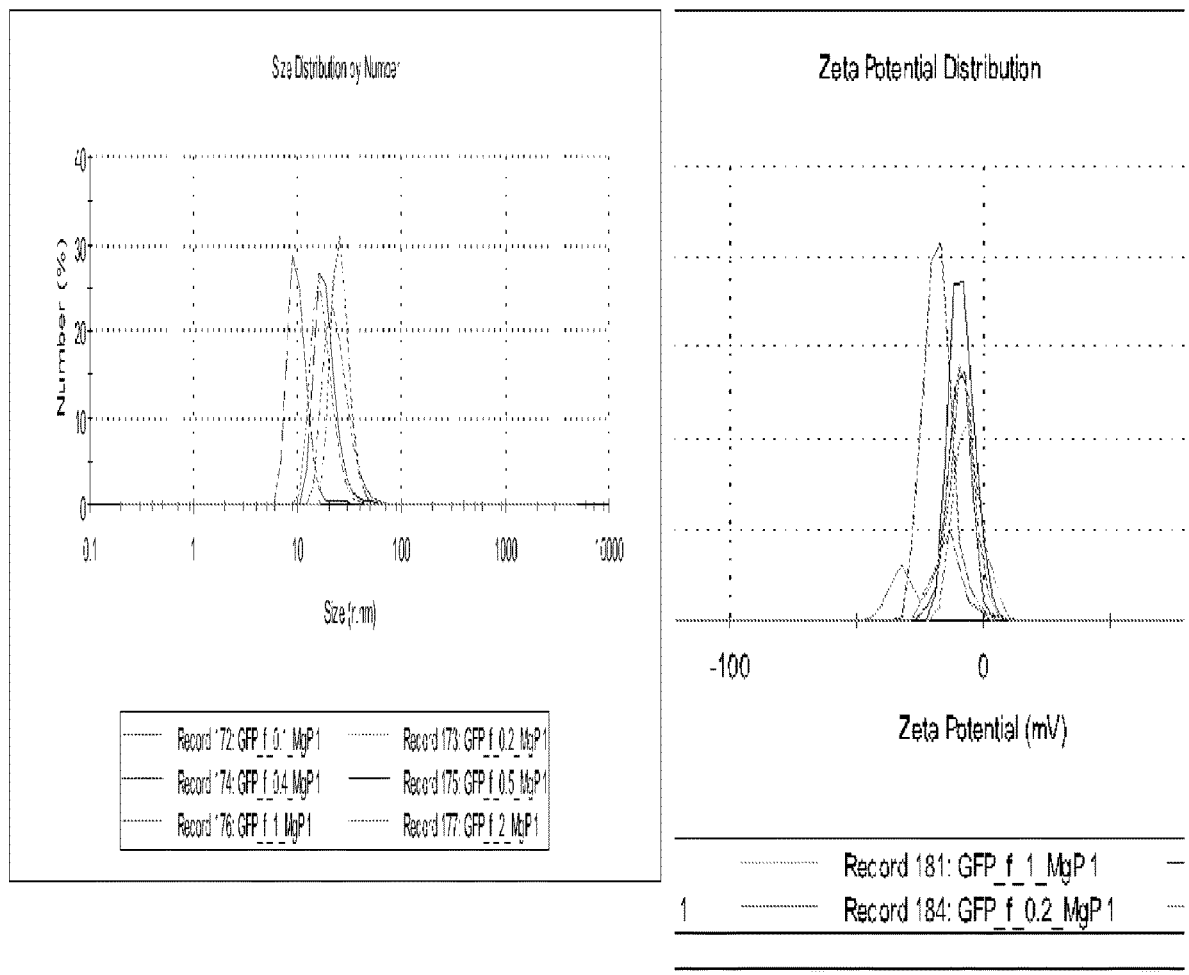
FIG. 6, through graphics, presents physical data on a nanoparticle embodiment with a magnesium core. Size distribution of particle from six different batches is shown in the upper left graph and zeta potential distribution of those batches is shown in the lower left graph. The table on the right shows the average size and zeta potential of those six batches.

Analytical data including the size and zeta potential distribution of the nanoparticles loaded with GFP plasmid is shown in FIG. 6. For the six records shown, the average diameter including the shell ranges from about 10 to about 25 nm, and the average zeta potential ranges from about −6.0 to about −18.0 mV.

Figure 7:
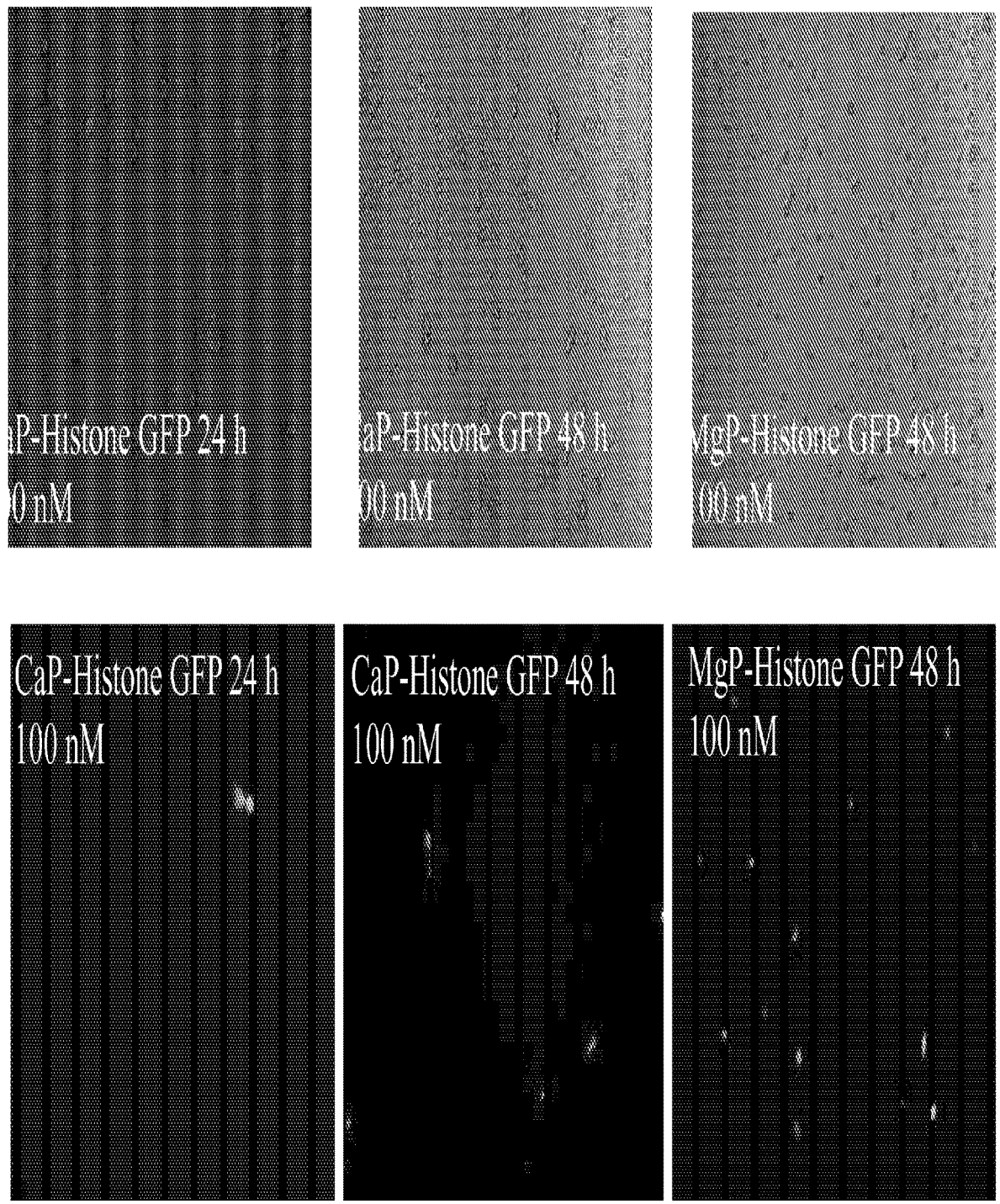
FIG. 7 consists of photographic images of fluorescence resulting from the transfection of GFP plasmid in cells from an SW480 cell line using calcium or magnesium phosphate cores of the invention with a histone coating. Images display a 24 h and 48 hour transfection period.

Fluorescence results are shown in FIG. 7 where photos in the lower row show green fluorescence spots, indicating successful GFP expression 48 hours after the transfection using the nanoparticle of the present invention as an in vitro delivery vehicle in a SW480 cell line.

Figure 8:
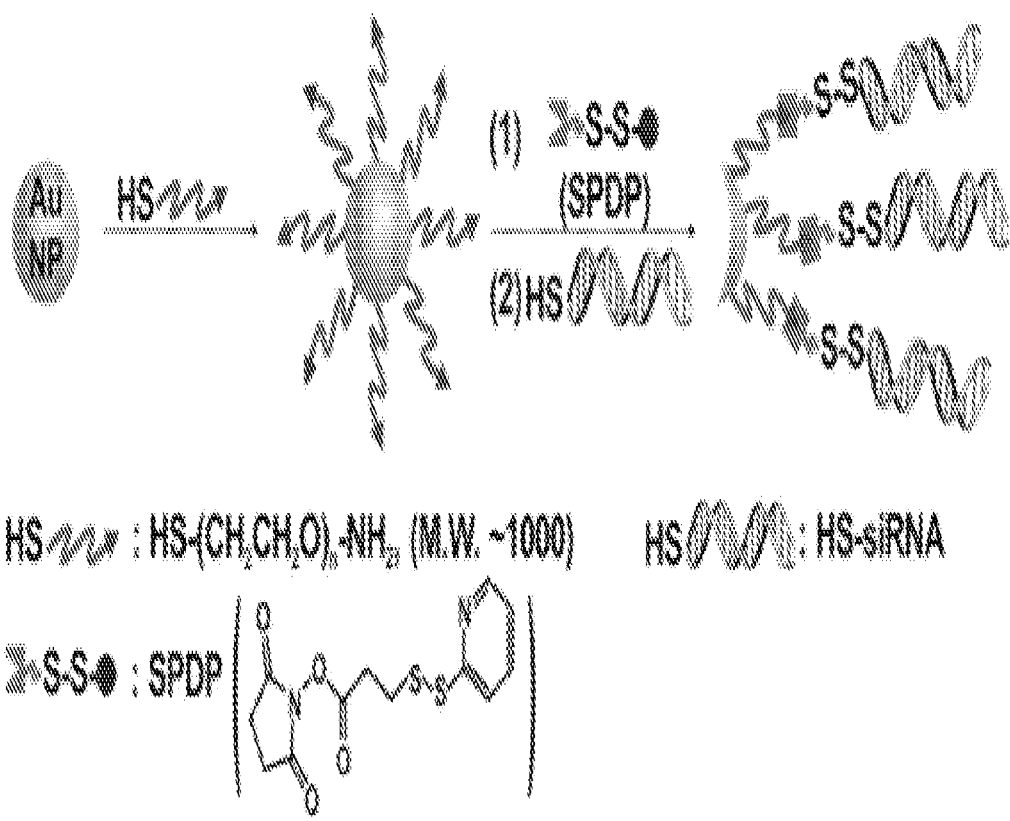
FIG. 8 schematically illustrates an exemplary method for making a gold nanoparticles and loading it with aiRNA according to an embodiment of the present invention.
Figure 9:
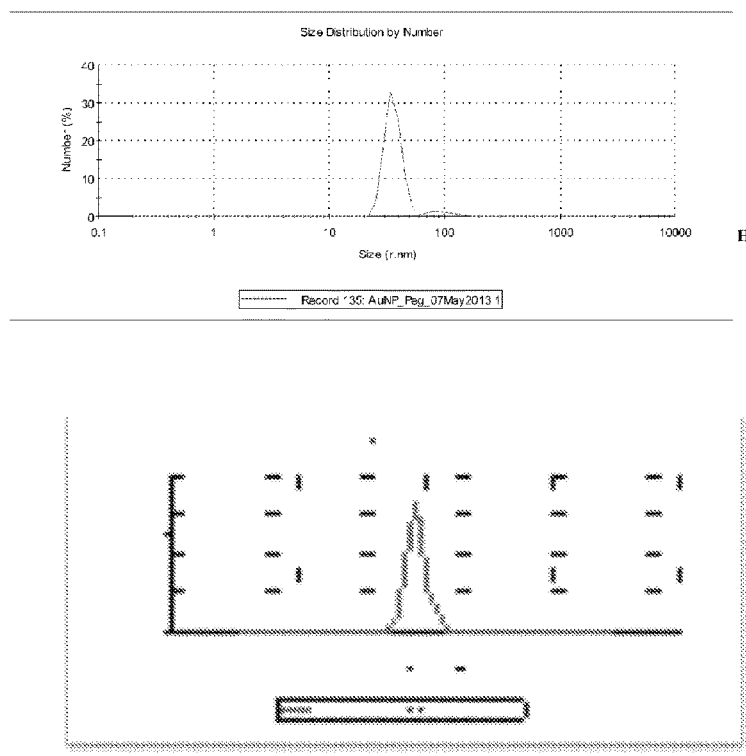
FIG. 9, through graphics, presents physical data on a gold nanoparticle embodiment, which is schematically shown on the right before conjugation to aiRNA takes place as outlined in FIG. 8. Size distribution of the particle is shown in the upper left graph and zeta potential distribution is shown in the lower left graph.
Figure 9:
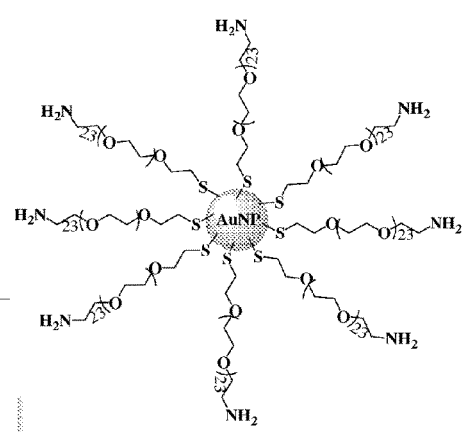

Example 2: aiRNA Delivery Using Gold Nanoparticles Results in Gene Silencing In Vitro Referring to FIG. 8, which illustrates the steps for conjugating aiRNA to a gold nanoparticle according to an embodiment of the present invention. First, commercially available gold nanoparticles were first PEGylated, i.e., functionalized with PEG chains through surface modification. The size distribution and zeta potential distribution of the modified gold nanoparticles are shown in FIG. 9, along with a schematic drawing of the modified nanoparticle. The PEGylated gold nanoparticles were about 19 nm in diameter on average. The average zeta potential for gold nanoparticle was about −8.53 mV before modification and about −7.29 mV after.

Figure 10:
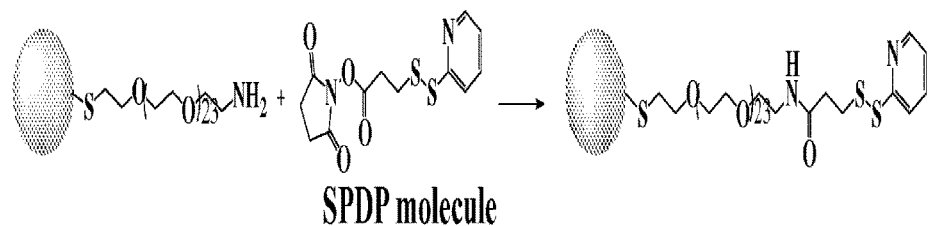
FIG. 10 schematically illustrates how the gold nanoparticle shown in FIG. 9 can be conjugated to an aiRNA molecule.
Figure 10:
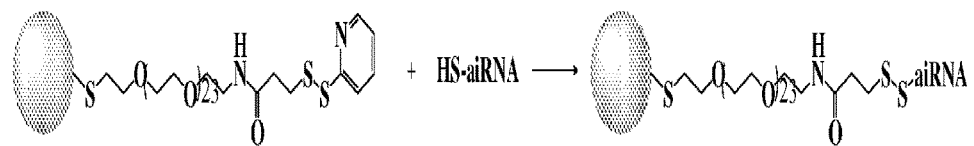

Referring back to FIG. 8, after the gold nanoparticles had been PEGylated, they were further modified in order to form a disulfide bond with the medically useful agent, aiRNA. First, the PEGylated gold nanoparticle was cross-linked with succinimidyl 3-(2-pyridyldithio)propionate (SPDP) molecules, making it capable to form a disulfide bond. Next, the nanoparticle was introduced to a modified aiRNA where its thiolate was exposed. As a result, the aiRNA became loaded onto the gold nanoparticle with the formation of a new disulfide bond between the two. Details of this step are further illustrated in FIG. 10.

Figure 11:
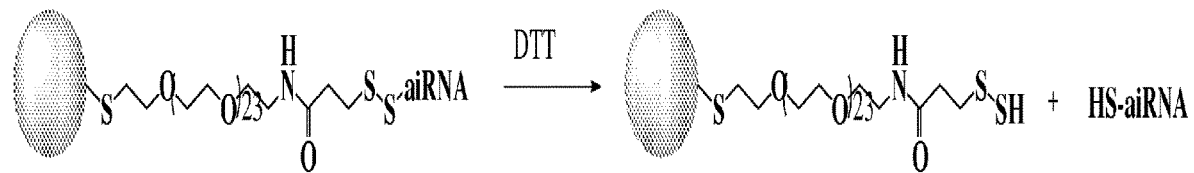
FIG. 11 schematically illustrates how aiRNA molecule can be released from the gold nanoparticle shown in FIG. 10.

Referring now to FIG. 11, to release the conjugated aiRNA from the gold nanoparticle, the disulfide bond was reduced using DTT. A ribogreen assay was used to quantify the concentration of aiRNA released following the reduction of the disulfide bond and C was about 4.12-5.2 µg/ml of aiRNA release from the gold nanoparticle.

Figure 12:
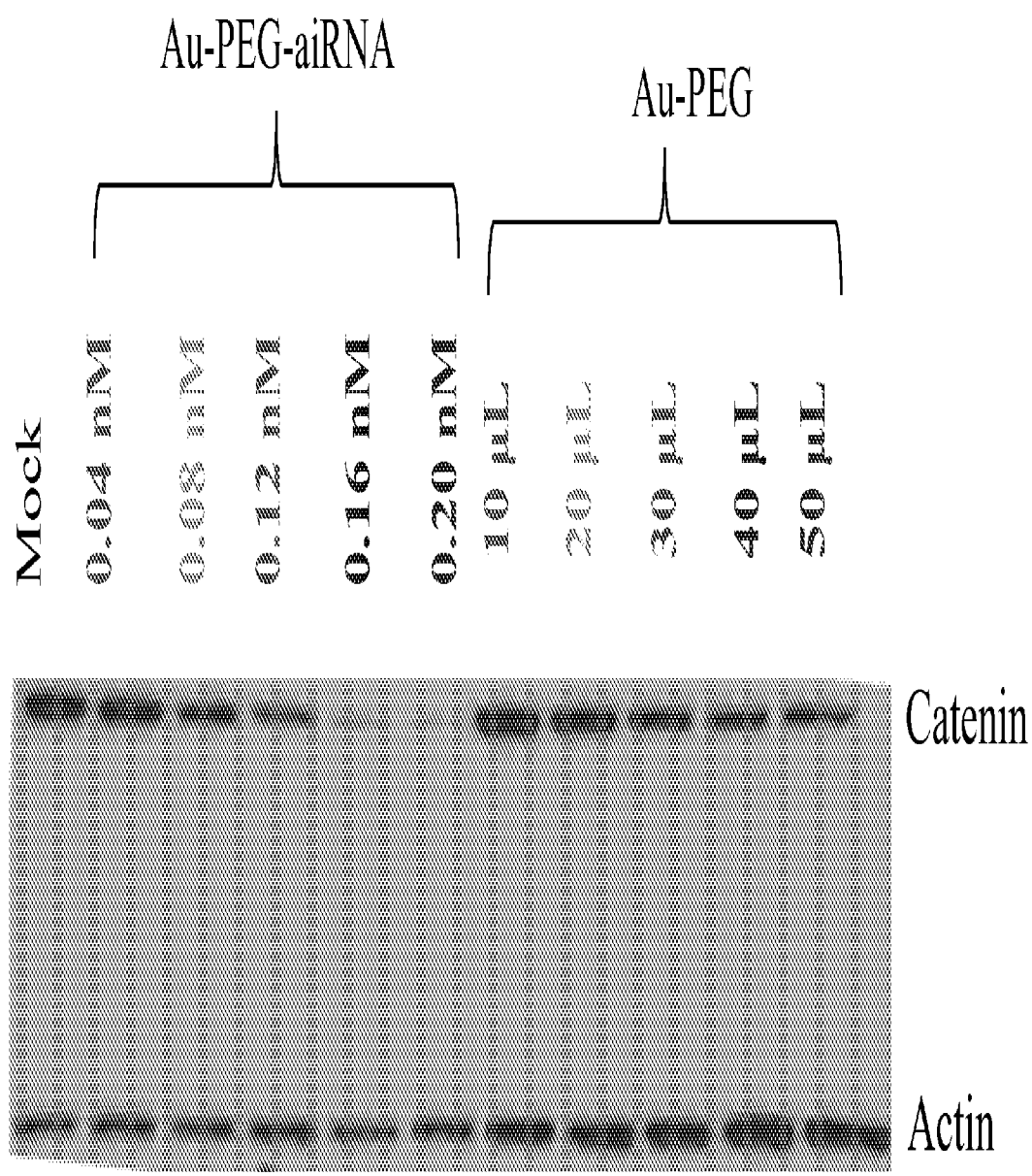
FIG. 12 is an image of a Western blot gel electrophoresis comparing gene silencing efficacy between unloaded PEGylated gold nanoparticle and those loaded with aiRNA. Concentration for unloaded gold nanoparticles was $3.17 \times 10^{-10}$ M.

FIG. 12 shows delivery efficacy of the gold nanoparticle prepared using the method described above in this example. An aiRNA of the following sequence and designed to silence the β-Catenin expression was conjugated to gold nanoparticles as described above:

```
                                        (SEQ ID NO: 1)
          5'-CACAAGAUGGAAUUU-3'

(SEQ ID NO: 2)
       3'-AAUAAAUUCCAUCUUGUGAUC-5'
```

A solution containing 10× histone (w/w in relation to the aiRNA) and 1% (v/v) TWEEN®-80 was added to the gold nanoparticles to coat them with a shell. As shown in the figure, the loaded nanoparticles showed significantly more gene silencing effect in vitro against the target, β-Catenin, than unloaded nanoparticles.

Example 3: aiRNA Delivery Using Magnesium Phosphate Nanoparticles with Polymer-Based Shell Achieves Gene Silencing In Vitro MgP cores loaded with aiRNA were prepared largely using the double-emulsion process described above. Specifically:

In each of vials A and B, 5 mL of cyclohexane/Igepal CO-520 solution (71/29 v/v) was prepared from reagents respectively available from EMD and Sigma. Meanwhile, aiRNA was dispersed in 1× RNAse-free buffer to make the desired concentration (e.g., about 5 µg/L). A volume of aiRNA (e.g., about 50 µg) was mixed with 100 µL of 500 mM MgCl$_2$. Then, the MgCl$_2$-aiRNA solution was added drop-wise to the oil/surfactant solution in vial A to form a well-dispersed emulsion without reverse micro-emulsion.

In vial B, 100 µL of 25 mM Na$_2$HPO$_4$ (pH=9) was added drop-wise to the oil/surfactant solution. The contents of vials A and B were then mixed and stirred for 30 minutes at room temperature. Afterwards, the contents were transferred into 10 centrifuge tubes (1.5 mL) and centrifuged for 30 minutes at 13,000 g. Supernatant was discarded and the pellet was washed with absolute ethanol (1 mL) twice. After the alcohol was removed, the resulting pellet was air-dried for 3-4 hours.

A polymer-based shell was coated onto the MgP nanoparticle cores already loaded with aiRNA. Specifically, biodegradable Polymers, Peg(5 k)-Poly-L-Lysine (10 U), Poly-L-Arginine (50 U) were coated onto the cores at a polymer ratio of 2.5:1 (PLL:PLR) & a complex ratio of 2.5:1 (polymer:aiRNA).

Figure 13:
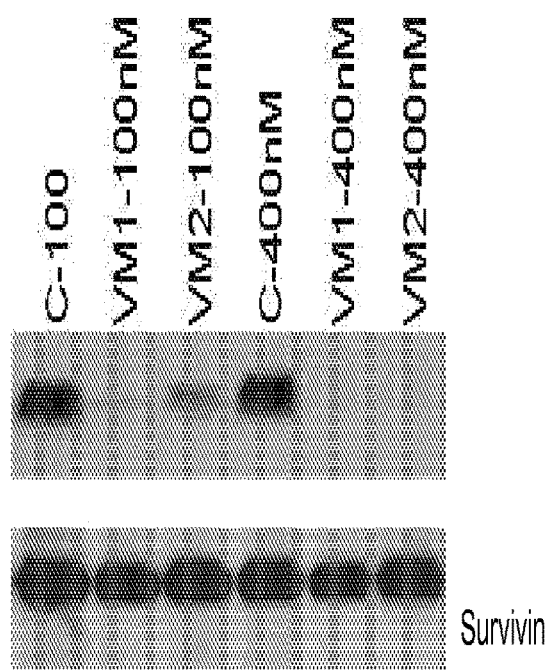
FIG. 13 illustrates in vitro gene silencing effect achieved through delivering aiRNA using a magnesium phosphate-based nanoparticle with a polymer-based shell. Left side is an image of a Western blot gel electrophoresis where the first and fourth lanes, counting from the left, are negative controls (unloaded nanoparticles) and the rest of the lanes are nanoparticles loaded with aiRNA of various concentrations. Upper right side schematically illustrates the composition of the loaded nanoparticle. Lower right side is a chart showing analytical data of the nanoparticles.
Figure 13:
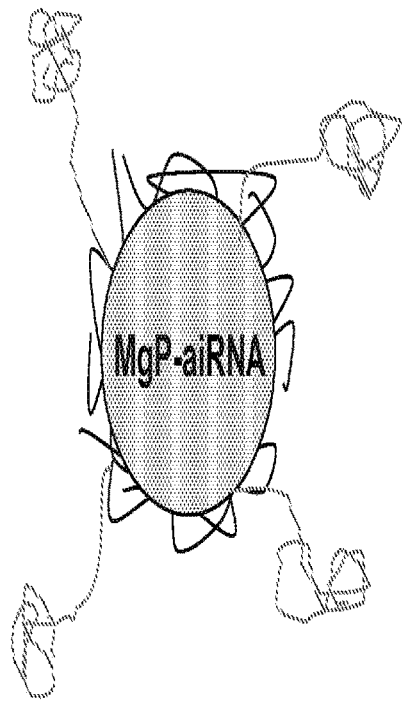

Referring to FIG. 13, physical and pharmacological data for the resulting nanoparticles are shown on the right side. For instance, average size of the nanoparticles was about 70 nm (and about 80 nm in other experiments, but certainly below 200 nm or 100 nm) and the surface charge was about +25 mV. The nanoparticles of the present invention exhibited good plasma stability, and cellular uptake and endosomal escape (data not shown) were both achieved.

Because in vitro effect has always been difficult to observe with nanoparticle vehicles, it was particularly encouraging to observe strong gene silencing effect (80-90%) as shown on the left side of FIG. 13. The cell lines tested included SW480 and DLD1 cells (human colon and colorectal cancer cell lines). The protein expression targeted by the aiRNA was survivin, and the aiRNA has the following sequence (as is true for other examples where survivin was targeted unless noted otherwise):

```
                                        (SEQ ID NO: 3)
        5'-GAUCAACAUUUUCAA-3'

(SEQ ID NO: 4)
        3'-AAUUUGAAAAUGUUGAUCUCC-5'
```

Example 4: aiRNA Delivery Using Magnesium Phosphate Nanoparticles with Albumin-Based Shell Achieves Gene Silencing In Vitro MgP cores loaded with aiRNA were prepared using the double-emulsion process described in the previous Example. A protein/peptide-based shell was coated onto the MgP nanoparticle cores already loaded with aiRNA. Specifically, human serum albumin (10%) was coated onto the cores.

Figure 14:
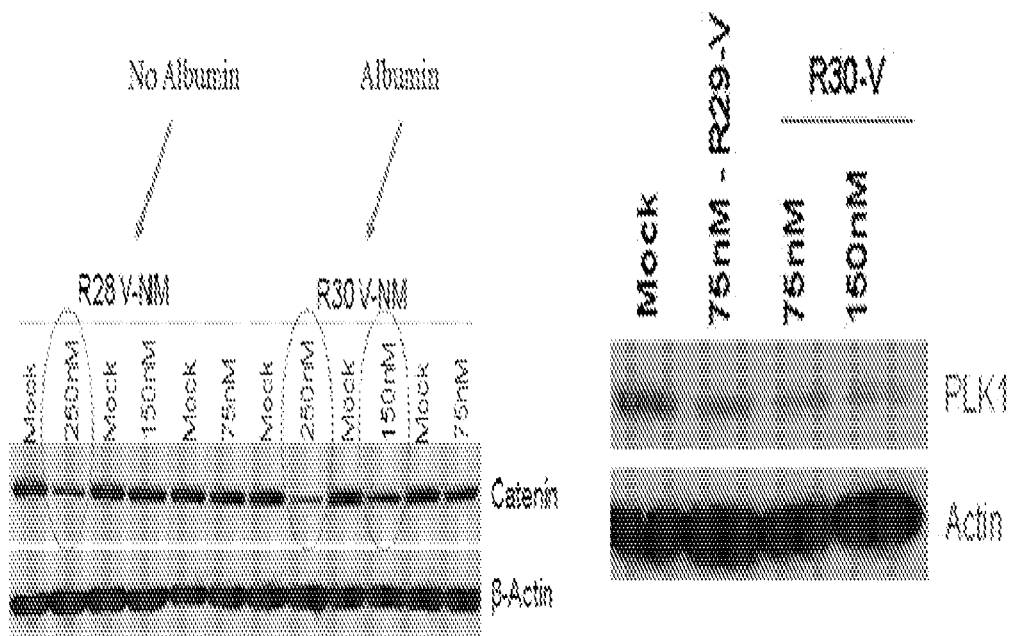
FIG. 14 illustrates in vitro gene silencing effect achieved through delivering aiRNA using a magnesium phosphate-based nanoparticle with a protein/peptide-based shell. The protein was albumin. The upper row consists of images of two Western blot gel electrophoreses (left one detects β-catenin and the right one detects PLK1). Lower right side is a chart showing analytical data of the nanoparticles.

Physical and pharmacological data for the resulting nanoparticles are shown in FIG. 14. For instance, average size of the nanoparticles was about 25-35 nm and the surface charge was about −8 to −12 mV. The nanoparticles exhibited good plasma stability, and cellular uptake and endosomal escape (data not shown) were both achieved.

Gene silencing effect (75-85%) was observed as summarized on the left side of FIG. 14. The cell lines tested included SW480. The expression of two proteins were targeted here by the aiRNA: β-Catenin, and PLK1 (polo-like kinase 1), respectively. PLK1 is a proto-oncogene implicated in a variety of cancers including colon and lung cancers, The aiRNA sequences used to target β-Catenin were the same as described above as SEQ ID NOS: 1 and 2. And the aiRNA sequences used to target PLK1 are as follows (as is true for other examples where PLK1 was targeted unless noted otherwise):

```
                                        (SEQ ID NO: 5)
        5'-GAUCACCCUCCUUAA-3'

(SEQ ID NO: 6)
        3'-AAUUUAAGGAGGGUGAUCUUC-5'
```

Example 5: 2'-O-Me-aiRNA Delivery Using Magnesium Phosphate Nanoparticles with Albumin-Based Shell Achieves Gene Silencing In Vitro and In Vivo Oligonucleotides with a methyl group at the 2'-OH residue of the ribose molecule can be advantageous in various applications. Among other things, 2'-O-Me-RNAs show the same behavior as DNA, but are more stable as they are protected against nuclease degradation. They also form more stable hybrids with complementary RNA strands compared to DNA or RNA.

Figure 15:
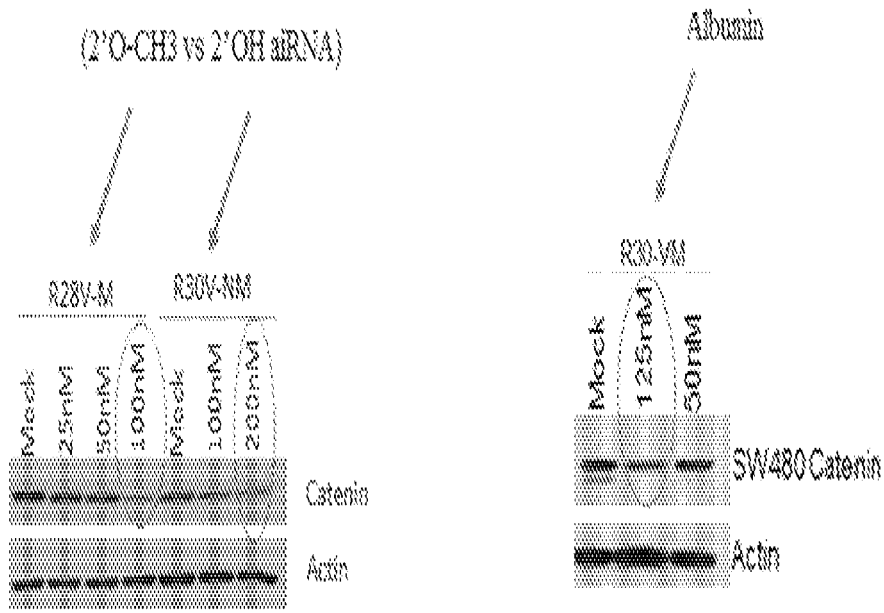
FIG. 15 illustrates in vitro and in vivo gene silencing effects achieved through delivering modified aiRNA (2'-O-Me-aiRNA) using a magnesium phosphate-based nanoparticle with a protein/peptide-based shell. The protein was albumin. The upper row consists of images of two Western blot gel electrophoreses showing effective suppression of β-catenin through delivery of 2'-O-Me-aiRNA. The lower row graphically illustrates in vivo efficacy observed in SW480 xenograft.
Figure 15:
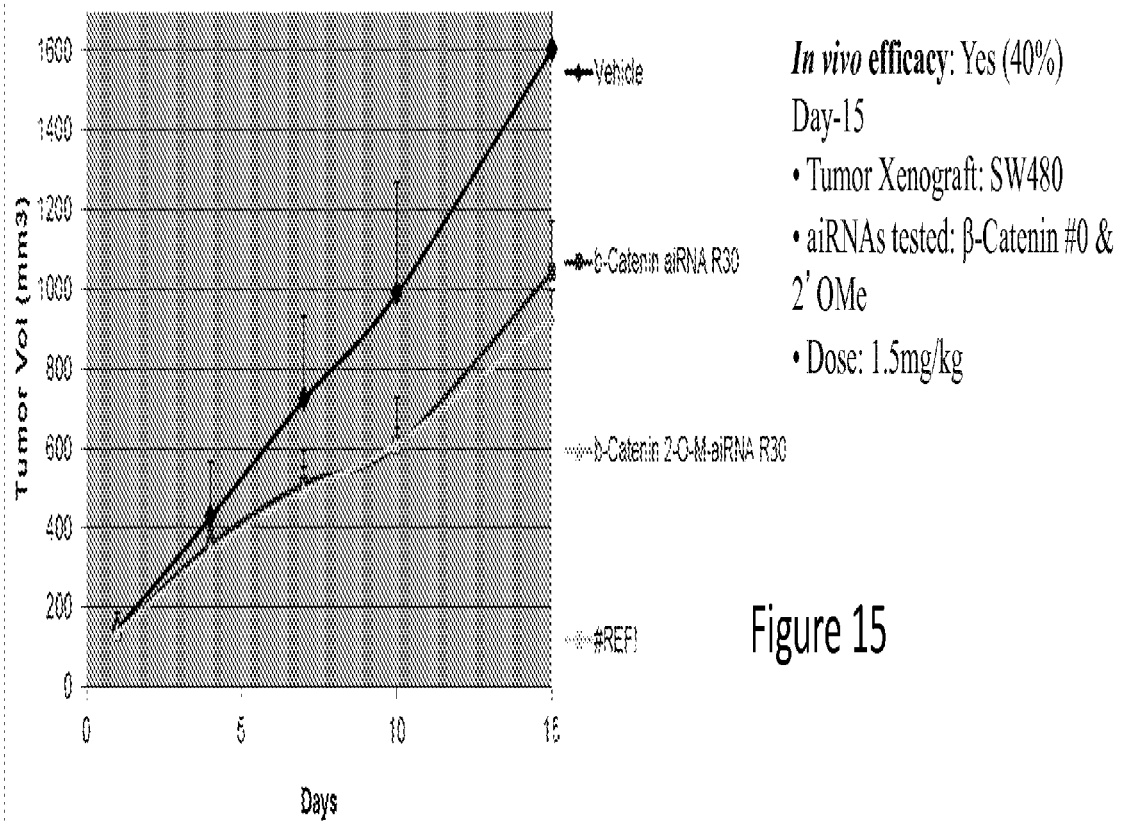

Nanoparticles with a core using only magnesium phosphate and further coated with an albumin-based shell were used to successfully deliver 2'-O-Me-aiRNAs to suppress targeted gene expression both in vitro and in vivo. The data is presented in FIG. 15. The aiRNA sequences used to target β-Catenin were the same as described above as SEQ ID NOS: 1 and 2 except nucleotides at certain selected positions in the sequence were modified with a 2'-OH methyl group.

Example 6: aiRNA Delivery Using Magnesium Phosphate Nanoparticles with Histone-Based Shell Achieves Gene Silencing In Vitro MgP cores loaded with aiRNA were prepared using the double-emulsion process described in the previous Examples. A protein/peptide-based shell was then coated onto the MgP nanoparticle cores already loaded with aiRNA. Specifically, 7× human histone mixed with 5× calf histone (w/w, in relation to the aiRNA load) were coated onto the cores.

Figure 16:
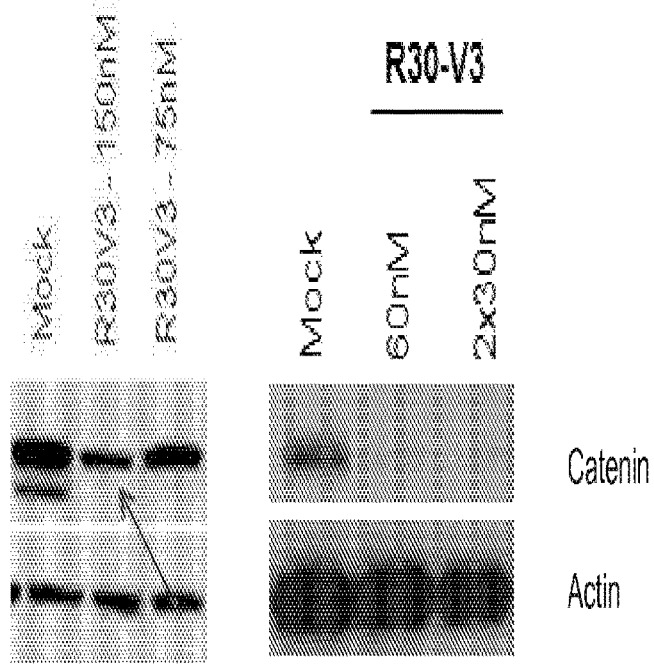
FIG. 16 illustrates in vitro gene silencing effect achieved through delivering aiRNA using a magnesium phosphate-based nanoparticle with a histone-based shell. Left side is an image of a Western blot gel electrophoresis showing suppression of β-catenin expression using nanoparticles loaded with the aiRNA of various concentrations. On the right side is a chart showing analytical data of the nanoparticles.

Physical and pharmacological data for the resulting nanoparticles are shown in FIG. 16. For instance, average size of the nanoparticles was about 15-25 nm and the surface charge was about +10 to +20 mV. The nanoparticles exhibited good plasma stability, and cellular uptake and endosomal escape (data not shown) were both achieved.

Gene silencing effect (65-75%) was observed as summarized on the left side of FIG. 16. The cell lines tested included SW480. The expression of β-Catenin was targeted here by the aiRNA.

Example 7: aiRNA Delivery Using Magnesium Phosphate Nanoparticles with Histone-and-Small-Peptide-Based Shell Achieves Gene Silencing In Vitro and In Vivo Nanoparticle cores consisting of MgP and loaded with aiRNA were prepared using the double-emulsion process described above.

A protein-and-small-peptide-based shell was coated onto the nanoparticle cores that were loaded with aiRNA. Specifically, 5× calf histone mixed with 3× small peptides (RGD) were coated onto the cores. Arginine-glycine-aspartic acid (RGD)-peptide is a tripeptide and can be used for cellular recognition akin to a targeting ligand.

Figure 17:
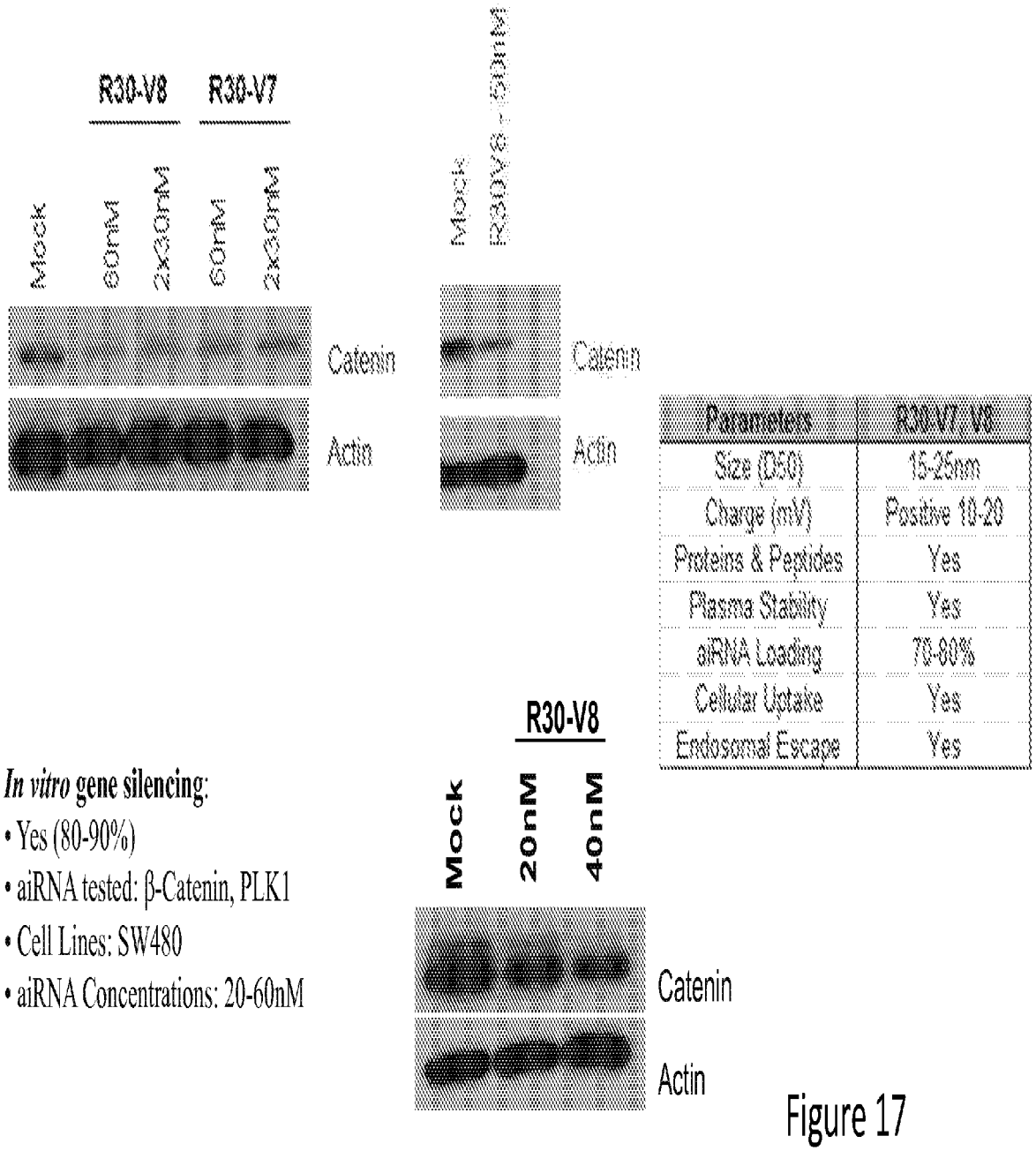
FIG. 17 illustrates in vitro gene silencing effect achieved through delivering aiRNA using a magnesium phosphate-based nanoparticle with a shell that includes both histone and a small peptide (RGD tripeptide). Included here are images of three Western blots showing suppression of β-catenin using nanoparticles loaded with aiRNA of various concentrations ("V7" was coated with cyclic RGD and "V8" linear RGD). On the right side is a chart showing analytical data of the nanoparticles.

Physical and pharmacological data for the resulting nanoparticles are shown in a chart in FIG. 17. For instance, average size of the nanoparticles was about 15-25 nm and the surface charge was about +10 to +20 mV. The nanoparticles exhibited good plasma stability, and cellular uptake and endosomal escape (data not shown) were both achieved.

Gene silencing effect (80-90%) was observed in vitro as summarized on the left side of FIG. 17. The cell lines tested included SW480. The expression of β-Catenin and PLK1 was targeted by respective aiRNAs. Both cyclic ("V7") and linear RGD ("V8") were tested.

Figure 18:
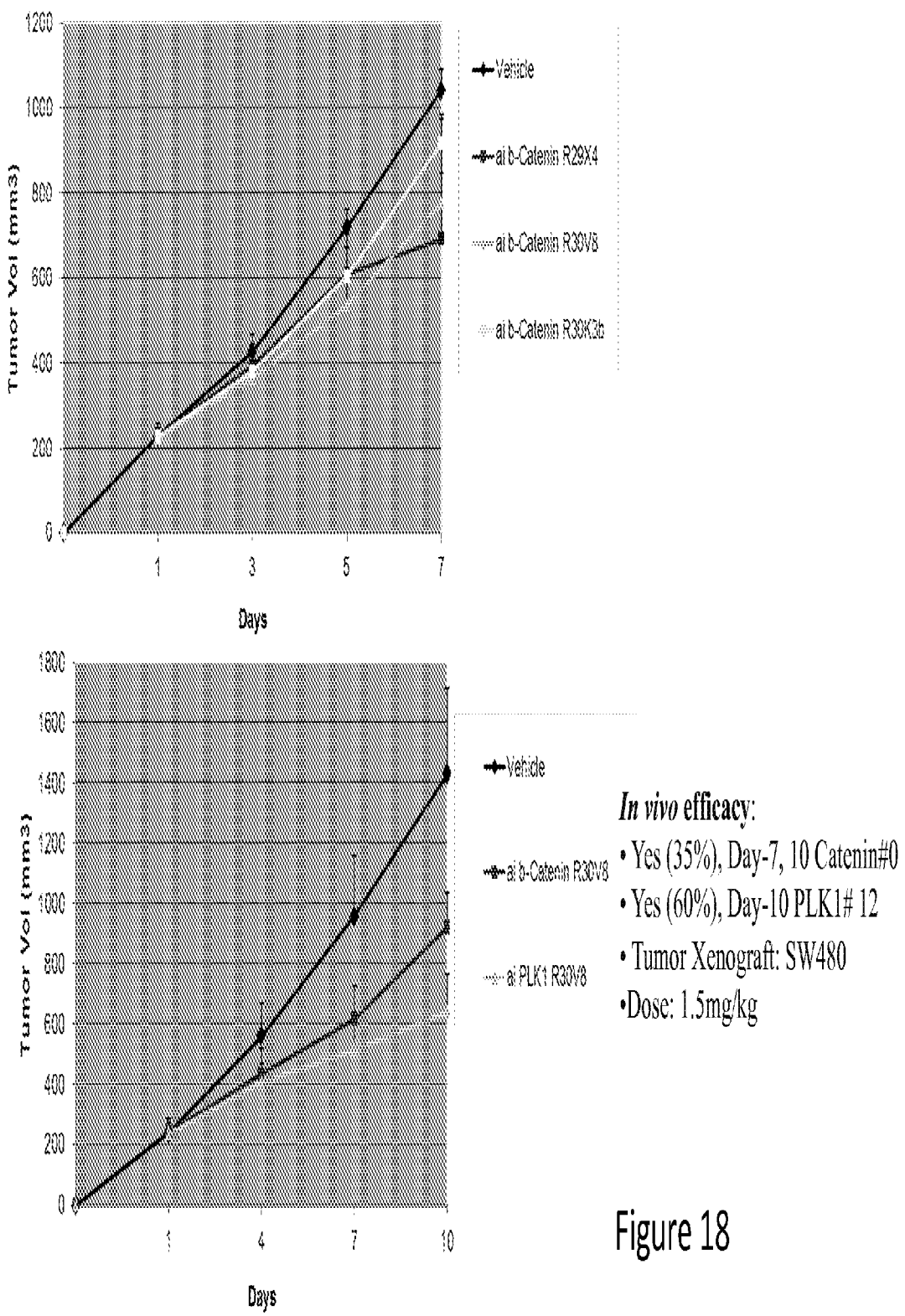
FIG. 18 illustrates in vivo gene silencing effect achieved through delivering aiRNA using a magnesium phosphate-based nanoparticle with a shell that includes both histone and a small peptide (RGD tripeptide).

Significant gene silencing effect was observed also in vivo as summarized on the right side of FIG. 18 (only data for nanoparticles coated with linear RGD is shown here). Tumor xenograft SW480 was tested on mice. The expression of β-Catenin and PLK1 was targeted by respective aiRNAs.

Figure 19:
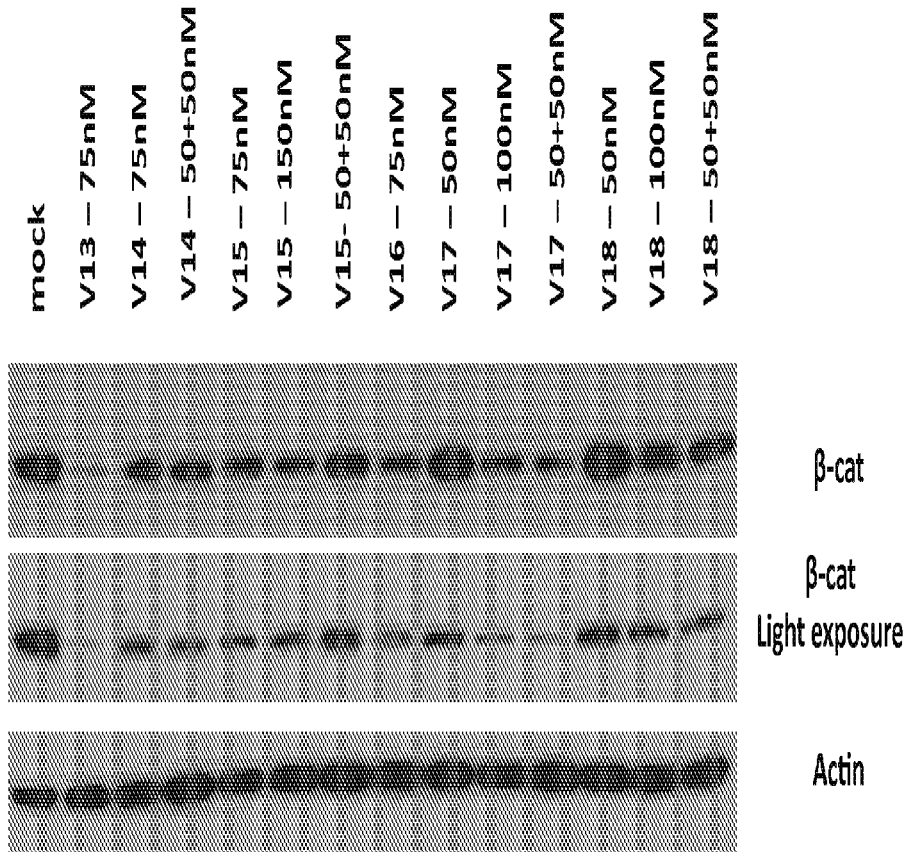
FIG. 19 illustrates varying degrees of in vitro gene silencing effect achieved through delivering aiRNA using a magnesium phosphate-based nanoparticle with a shell that includes both histone and a surfactant or RDG tripeptide.

Example 8: aiRNA Delivery Using Magnesium Phosphate Nanoparticles with Shells Including Differing Surfactants Nanoparticle cores consisting of MgP and loaded with aiRNA were prepared using the double-emulsion process described above. As shown in FIG. 19, for the shell/coating around the core, besides histone (5×), various surfactants were used including CREMOPHOR® EL, TWEEN®-80, TWEEN®-20, and TRITON®-X100 ("V13-16," respectively).

Results on in vitro gene silencing against β-Catenin were shown side-by-side with nanoparticles loaded with cyclic and linear RGD in the shell with histone. While the results were not uniform, varying degree of gene silencing could be seen.

Example 9: aiRNA Delivery Using Magnesium Phosphate Nanoparticles with Histone-and-CREMOPHOR®-Based Shell Achieves Gene Silencing In Vitro and In Vivo Nanoparticle cores consisting of MgP and loaded with aiRNA were prepared using the double-emulsion process described above. A protein-and-surfactant-based shell was coated onto the nanoparticle cores that were loaded with aiRNA. Specifically, 5× calf histone mixed with 5% CREMOPHOR® EL were coated onto the cores using methods described above.

Figure 20:
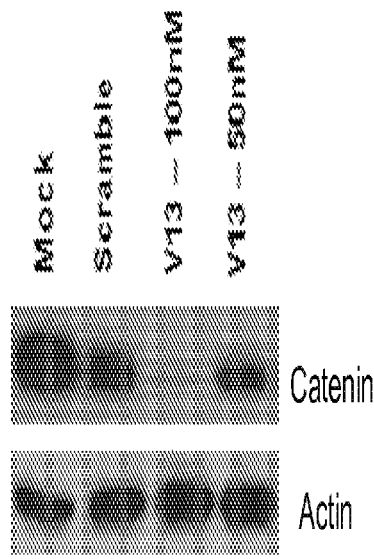
FIG. 20 illustrates in vitro gene silencing effect achieved through delivering aiRNA using a magnesium phosphate-based nanoparticle with a shell that includes both histone and CREMOPHOR® EL. Included here are images of three Western blots (left) showing suppression of β-catenin, PLK1, and Survivin using nanoparticles loaded with the aiRNA of various concentrations. On the right side is a chart showing analytical data of the nanoparticles.
Figure 20:
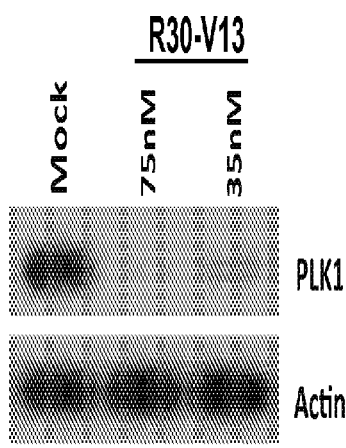
Figure 20:
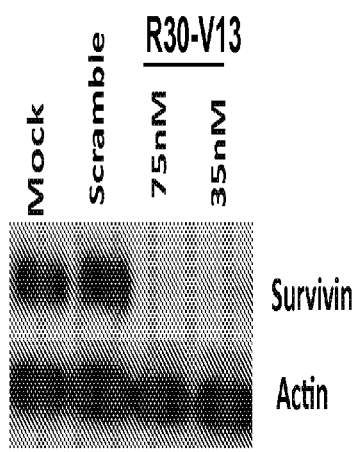

Physical and pharmacological data for the resulting nanoparticles ("V13") are shown in a chart in FIG. 20. For instance, average size of the nanoparticles was very small, at about 6-15 nm. Surface charge of the nanoparticles was about +5 to +12 mV. The nanoparticles exhibited good plasma stability, and cellular uptake and endosomal escape (data not shown) were both achieved.

Gene silencing effect observed in vitro and summarized on the left side of FIG. 20 was also excellent, reaching an impressive 85-98%. The cell lines tested included SW480. The expression of β-Catenin, PLK1 and Survivin was targeted by respective aiRNAs. Resulting Western blot images for each targeted protein is shown on the left side of FIG. 20. The aiRNA sequences used as scramble control are as follows (as is true for other examples unless noted otherwise):

```
                                          (SEQ ID NO: 7)
5'-GUAGUUAUAGUCGAU-3'

(SEQ ID NO: 8)
3'-AACAUCGACUAUAACUACCUG-5'
```

Figure 21:
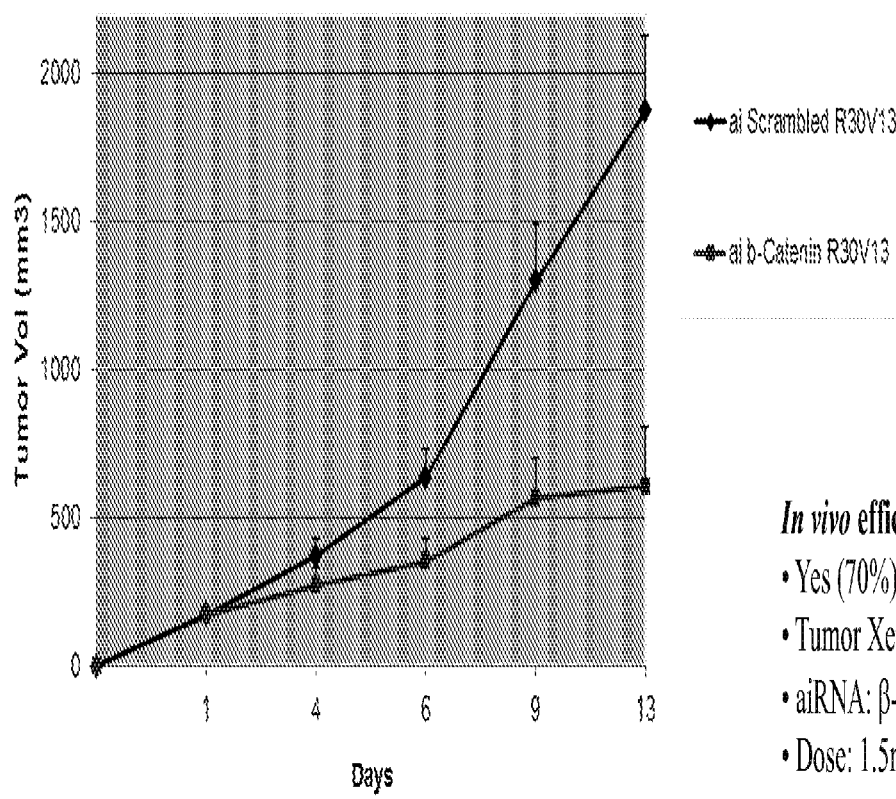
FIG. 21 illustrates in vivo gene silencing effect achieved through delivering aiRNA using a magnesium phosphate-based nanoparticle with a shell that includes both histone and CREMOPHOR® EL.

Significant gene silencing effect was observed also in vivo as illustrated in FIG. 21. Tumor xenograft SW480 was tested on mice. The expression of β-Catenin was targeted by aiRNA delivered with the magnesium phosphate nanoparticles coated with histone and CREMOPHOR®. As shown in FIG. 21, at Day-13 after dosing using the nanoparticles of the invention, significant inhibition on tumor growth was still evident.

Figure 22:
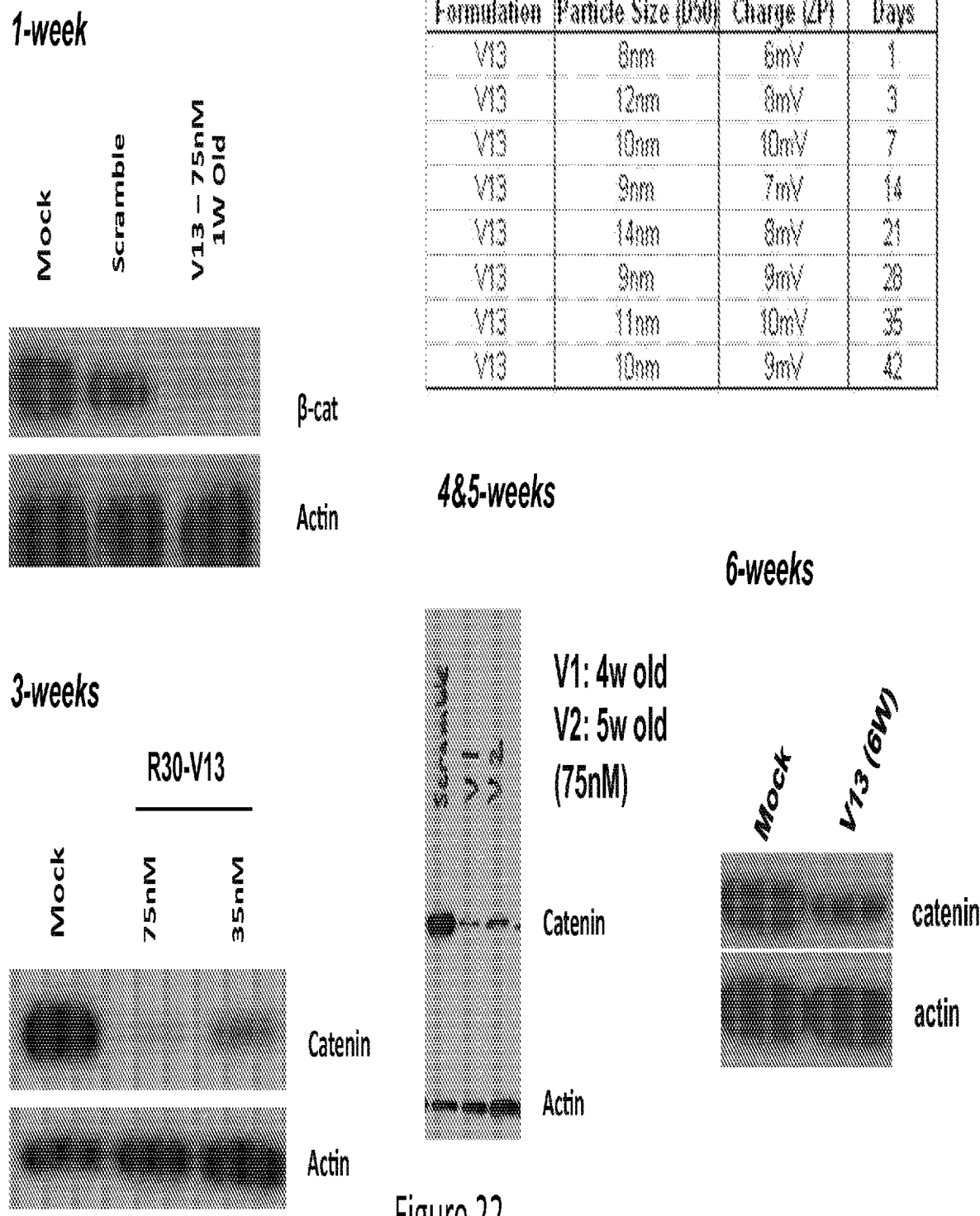
FIG. 22 includes four Western blot images showing in vitro gene silencing effect achieved through delivering aiRNA using a magnesium phosphate-based nanoparticle with a shell that includes both histone and CREMOPHOR® EL at various time points during storage. A chart summarizing particle sizes and charges of the nanoparticles during storage is also included.

This nanoparticle also exhibited enduring stability as illustrated in FIG. 22. Stored at 4° C., the "V13" nanoparticles largely maintained their original particle size and charges through the six weeks of time. Efficacy in inducing gene silencing also remained intact during the six weeks as gel picture taken at various time points show (FIG. 22). The "V13" nanoparticles also were stable enough to resist nuclease degradation after being left in 50% mouse plasma for two hours (data not shown). Various tests have also shown that "V13" nanoparticles can be lyophilized and reconstituted without significantly compromising their delivery capability or the efficacy of the medically useful agents they carry.

Example 10: aiRNA Delivery Using Magnesium Phosphate Nanoparticles with Protamine-and-CREMOPHOR® Based Shell Achieves Gene Silencing In Vitro MgP cores loaded with aiRNA were prepared using the double-emulsion process described in the previous Examples. A protein/surfactant-based shell was coated onto the MgP nanoparticle cores already loaded with aiRNA. Specifically, 7× protamine (w/w, in relation to the aiRNA load) mixed with 5% CREMOPHOR® were coated onto the cores.

Figure 23:
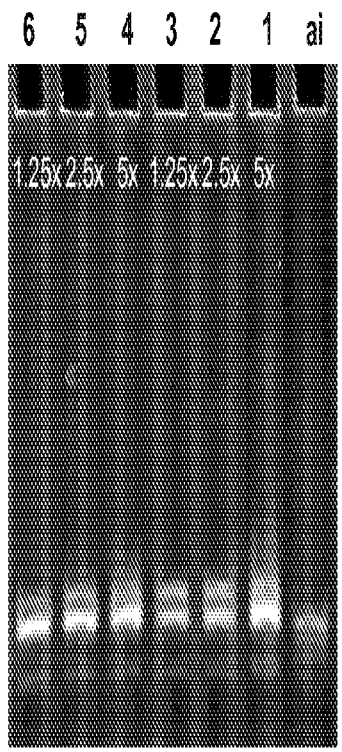
FIG. 23 includes a Northern blot image (left) showing resistance to nuclease digestion of aiRNA loaded onto a magnesium phosphate-based nanoparticle with a shell that includes both protamine and CREMOPHOR® EL. A chart showing analytical data of the nanoparticles is also included on the right.

Physical and pharmacological data for the resulting nanoparticles are shown in FIG. 23. For instance, average size of the nanoparticles was about 9-20 nm and the surface charge was about +5 to +18 mV. The nanoparticles exhibited good plasma stability, and cellular uptake and endosomal escape (data not shown) were both achieved.

As indicated by the gel picture in FIG. 23, the resulting nanoparticles also were sufficiently stable to resist nuclease degradation after being left in 50% mouse plasma for four hours.

Figure 24:
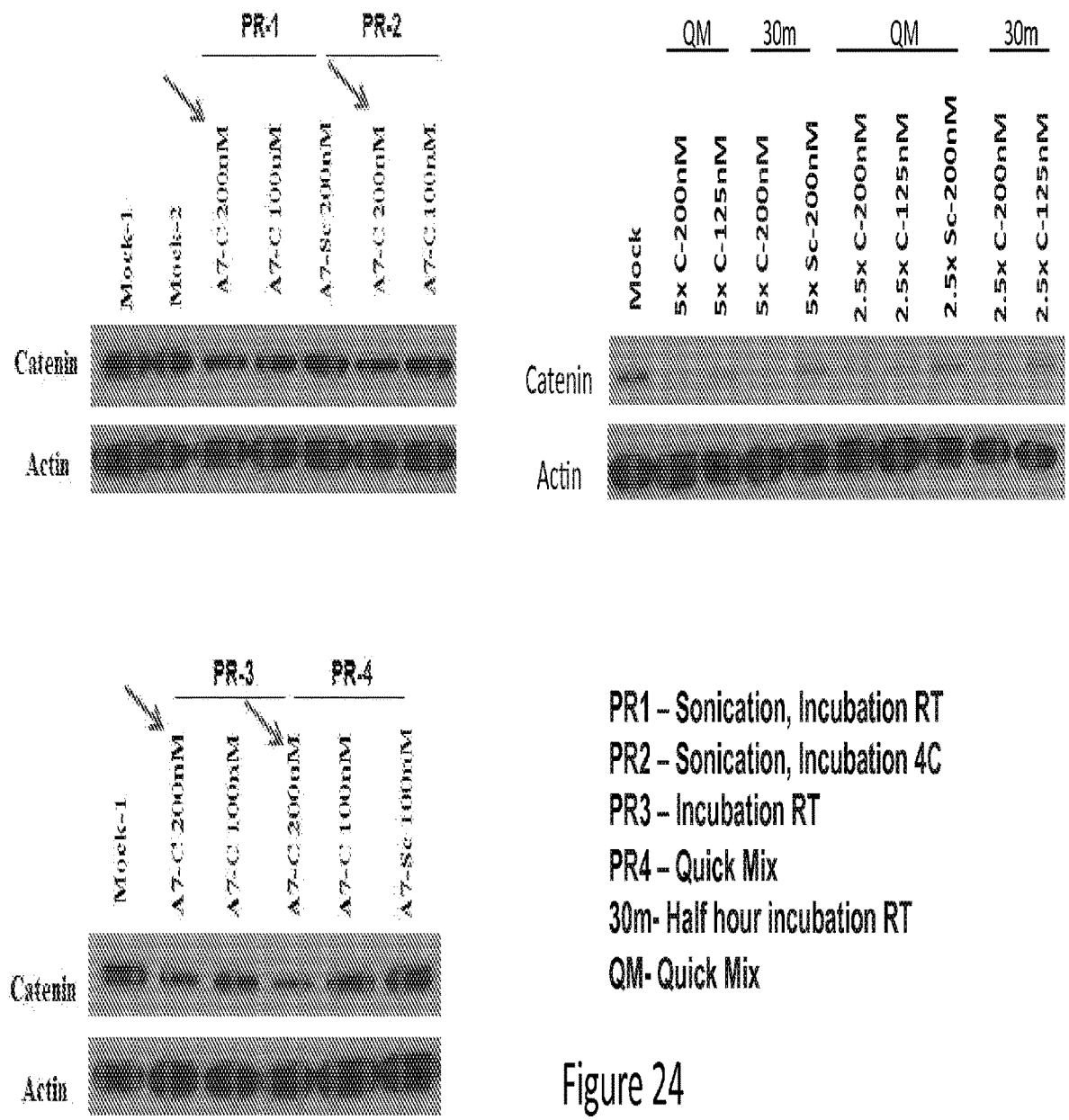
FIG. 24 illustrates in vitro gene silencing effect achieved through delivering aiRNA using a magnesium phosphate-based nanoparticle with a shell that includes both protamine and CREMOPHOR® EL. Included here are images of three Western blots showing suppression of β-catenin using nanoparticles loaded with the aiRNA where the specific steps for coating the nanoparticles as well as the nanoparticle concentrations were varied.

Gene silencing effect (70-80% in vitro) was observed as summarized on the top of FIG. 24. The cell lines tested included SW480. The expression of β-Catenin was targeted here by the aiRNA. Steps in adsorbing the coating solution onto the nanoparticle cores were varied to test the effect on delivery efficacy.

Example 11: aiRNA Delivery Using Magnesium Phosphate Nanoparticles with Protamine-and-CREMOPHOR®-Based Shell Achieves Gene Silencing In Vitro Nanoparticle cores consisting of MgP and loaded with aiRNA were prepared using the double-emulsion process described above. A protein-and-surfactant-based shell was coated onto the nanoparticle cores that were loaded with aiRNA. Specifically, a coating solution where 5× calf protamine (w/w in relation to the aiRNA load) was premixed with 5% CREMOPHOR® EL was added to the cores using methods described above. Optionally, the coating solution was added with 3.5% w/v hydroxypropyl beta cyclodextrin.

Figure 25:
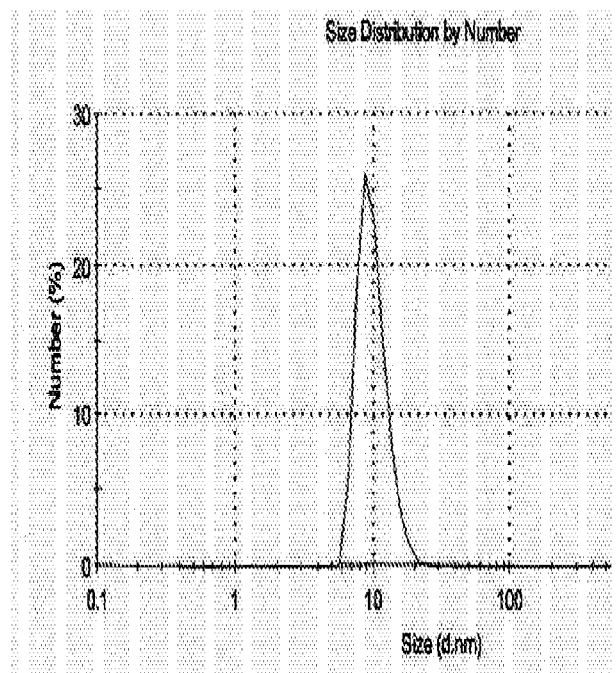
FIG. 25 shows data characterizing a magnesium phosphate-based nanoparticle with a shell that includes both protamine and CREMOPHOR® EL in comparison to the same nanoparticle except with the addition of cyclodextrin in the shell. Size distribution of nanoparticles of the "K7" composition (MgP with 5× protamine and 5% CREMOPHOR® EL) is also presented in the lower graph.

Physical and pharmacological data for the resulting nanoparticles ("K7" for shell formulation with protamine and CREMOPHOR®, and "K7C" for the same formulation with the addition of cyclodextrin) are shown in a chart in FIG. 25. For K7 nanoparticles, mean particle size was about 13-21 nm. Surface charge of the K7 nanoparticles was about +15 to +18 mV. For K7C nanoparticles, mean particle size was about 13-20 nm. Surface charges of the K7 nanoparticles ranged from about +14 to +16 mV.

The nanoparticles also exhibited good plasma stability, specifically, against human plasma or mice plasma (data not shown).

Gene silencing effect using the nanoparticles was observed in vitro in SW480 cells. Time course profile showed that single dose effect lasted until 72 hours after the administration for nanoparticles loaded with aiRNA targeting β-Catenin (data not shown).

Various other compositions for the shell around the Mg core could also achieve gene-silencing effect at least in vitro. These compositions included ones with various combinations of two surfactants in the shell selected from (data not shown): SOLUTOL® HS-15, TWEEN® 20, TWEEN® 80, TRITON® and CREMOPHOR®.

Figure 26:
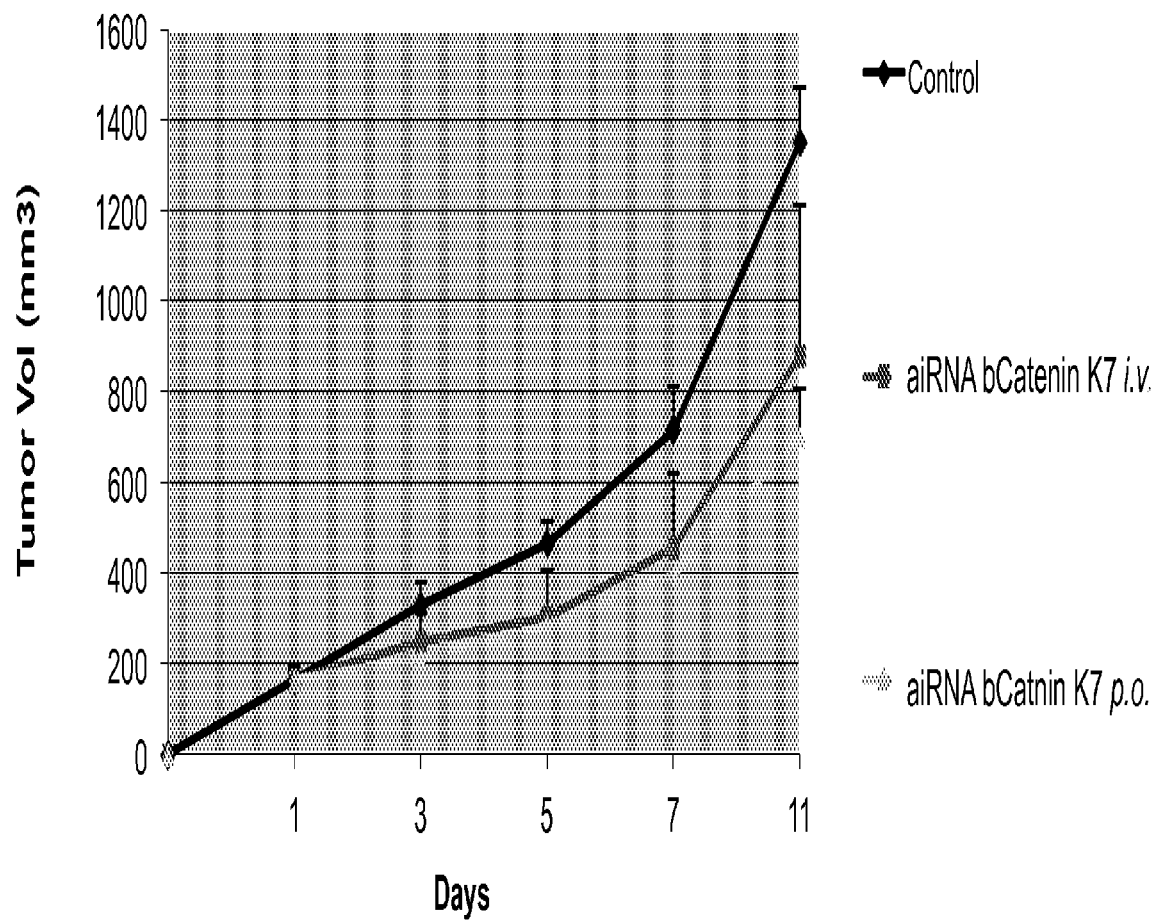
FIG. 26 compares in vivo effects on xenografted tumor (SW480) between an intravenous (i.v.) and an oral (p.o.) formulation for aiRNA (targeting β-catenin) carried by magnesium phosphate-based nanoparticle with a shell that includes both protamine and CREMOPHOR® EL ("K7" nanoparticles).

Example 12: Pharmaceutical Formulation Based on Magnesium Phosphate Nanoparticles with Protamine-and-CREMOPHOR®-Based Shell For K7 nanoparticles described above in Examples 10 and 11 (MgP core with protamine-and-CREMOPHOR®-containing shell), tumor inhibition effected through intravenous administration is compared with oral administration, as shown in FIG. 26. Both showed strong clinical effectiveness with both in vivo (FIG. 26) and in vitro data (not shown).

Figure 27:
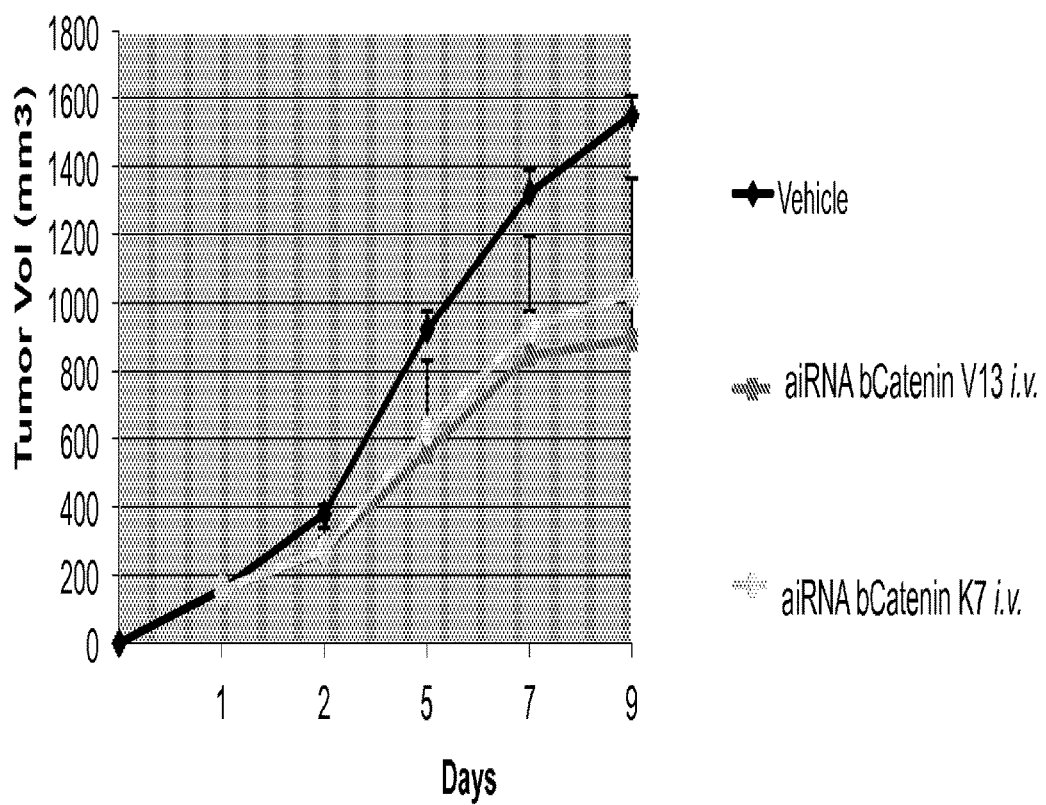
FIG. 27 illustrates in vivo effects on tumor by intravenous (i.v.) formulations for aiRNA (targeting β-catenin) carried by magnesium phosphate-based nanoparticle with a shell that includes (1) both histone CREMOPHOR® EL ("V13" nanoparticles); or (2) protamine and CREMOPHOR® EL ("K7" nanoparticles).

Example 13: Pharmaceutical Formulation Based on Magnesium Phosphate Nanoparticles with CREMOPHOR®-and-a-Small-Protein-Based Shell For V13 nanoparticles described above in Example 9 (MgP core with histone-and-CREMOPHOR®-containing shell) and K7 nanoparticles described above in Examples 10 and 11 (MgP core with protamine-and-CREMOPHOR®-containing shell), in vivo tumor inhibition was effected through intravenous administration (FIG. 27) as well as through oral administration. Both kinds of nanoparticles showed marked clinical effectiveness via either route of administration.

Figure 28:
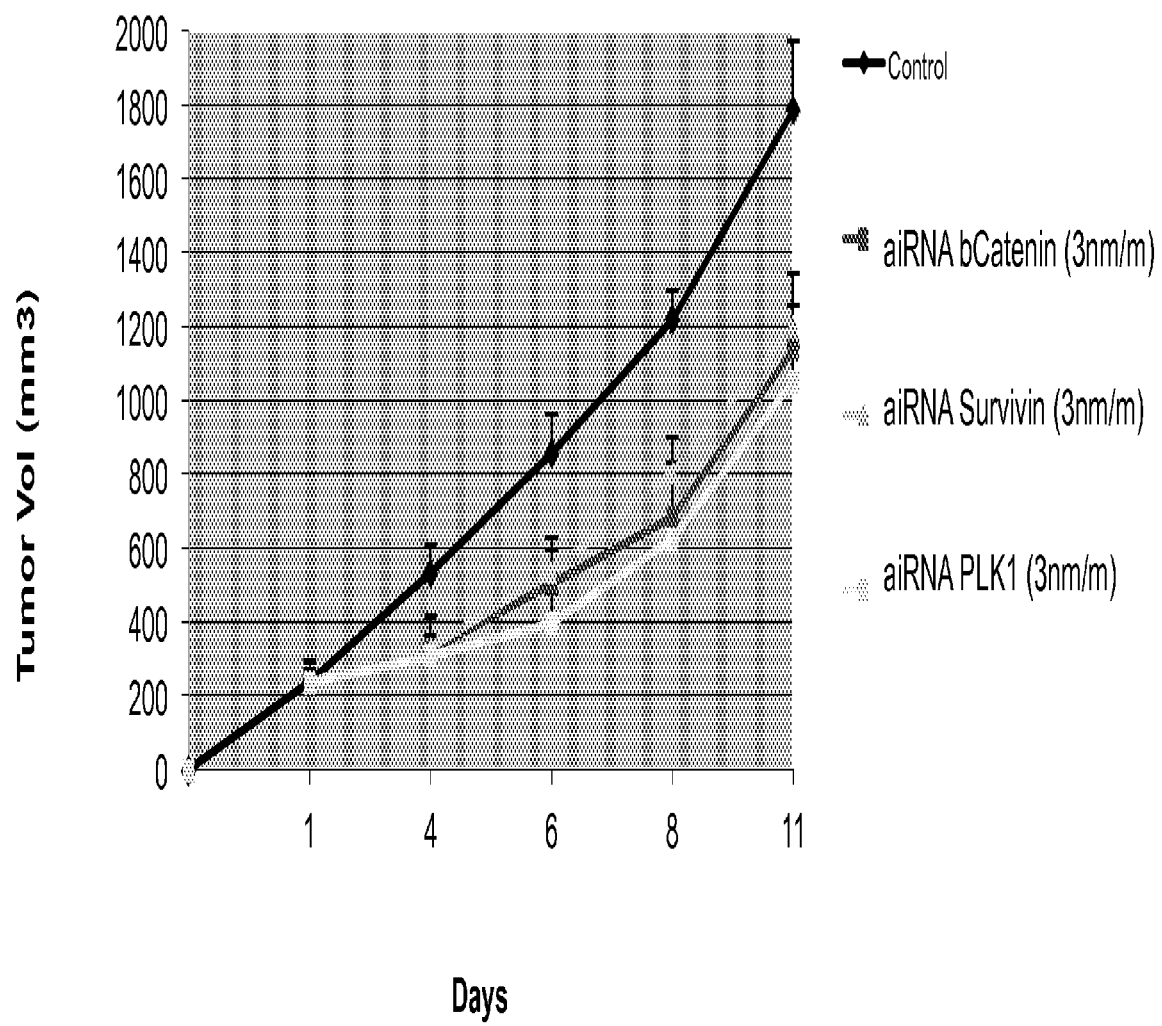
FIG. 28 illustrates data from further in vivo studies for effective anti-tumor regimen with intravenous (i.v.) formulations for aiRNA (targeting β-catenin, Survivin, and PLK1) carried by "K7" nanoparticles in SW480 cells.
Figure 29:
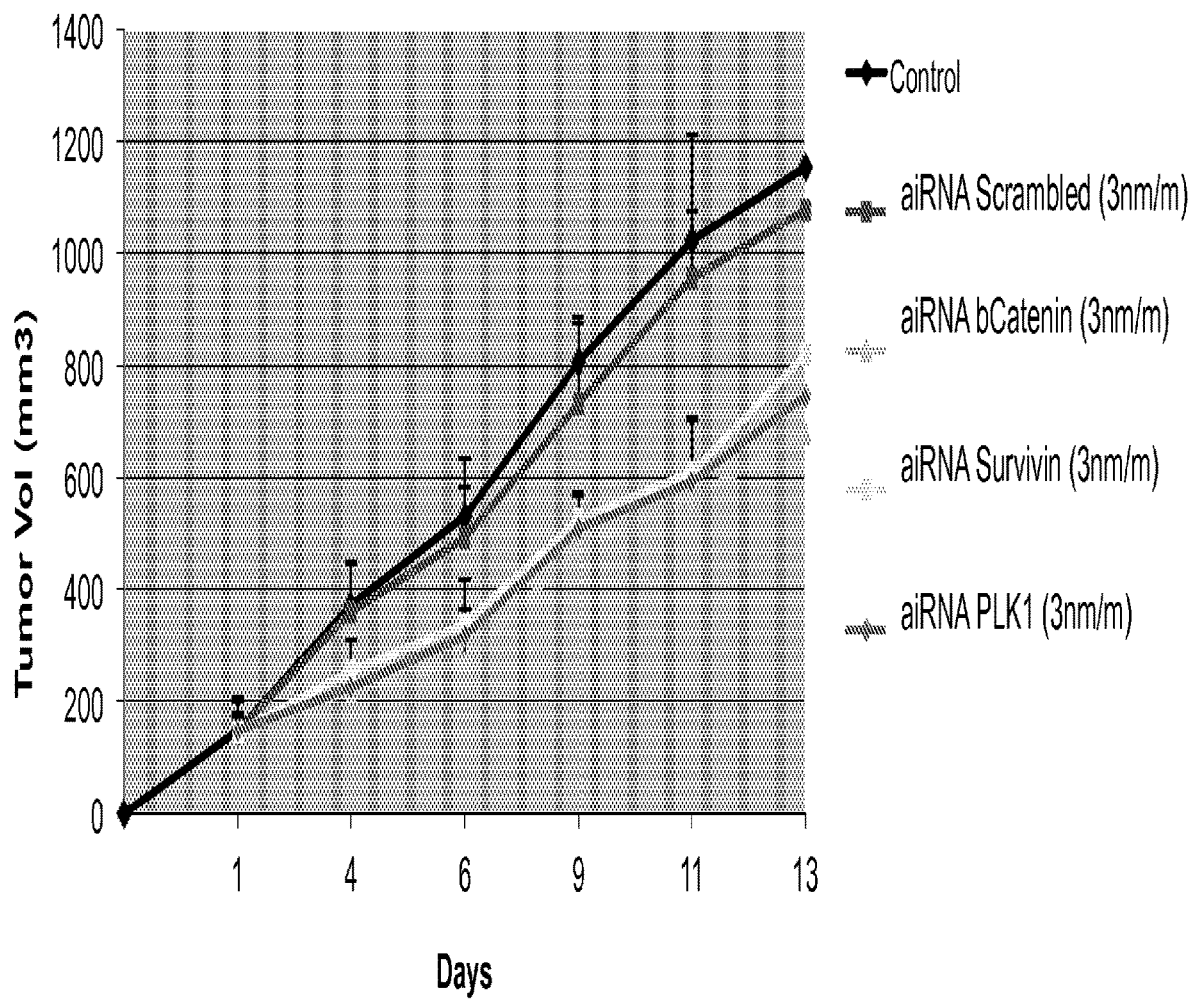
FIG. 29 illustrates data from further in vivo studies for effective anti-tumor regimen with intravenous (i.v.) formulations for aiRNA (targeting β-catenin, Survivin, and PLK1) carried by "K7" nanoparticles in mice transfected with human pancreatic cancer tumor xenograft.

Example 14: aiRNA-Lead Selection Using Magnesium Phosphate Nanoparticles with Protamine-and-CREMOPHOR®-Based Shell Using aiRNAs loaded onto K7 nanoparticles, which each has a MgP core surrounded by a protamine-and-CREMOPHOR®-containing shell, selection against various oncogenes or pro-oncogenes for viable pharmaceutical regimen were conducted in mice. Using this vehicle, previously tested intravenous (i.v.) formulations were tested against β-catenin, Survivin, and PLK1 expressions (FIG. 28). Effective inhibition of tumor growth was observed with both rapid onset and lasting effects against all three targets. Similar experiments were conducted in human pancreatic cancer xenograft with similarly impressive results observed (FIG. 29).

Example 15: Pharmaceutical Optimization

Figure 30:
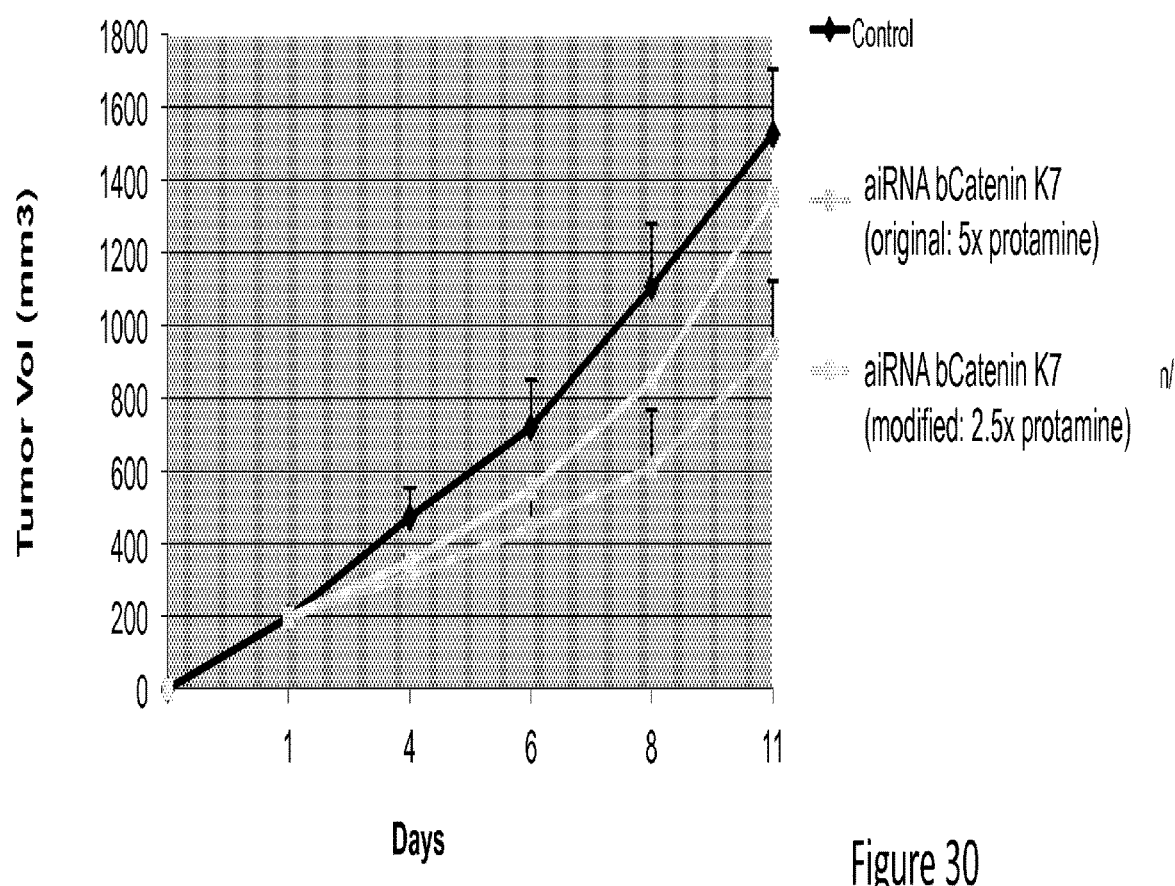
FIG. 30 illustrates data from in vivo studies for the most effective protamine concentration in the K7 formulation.
Figure 31:
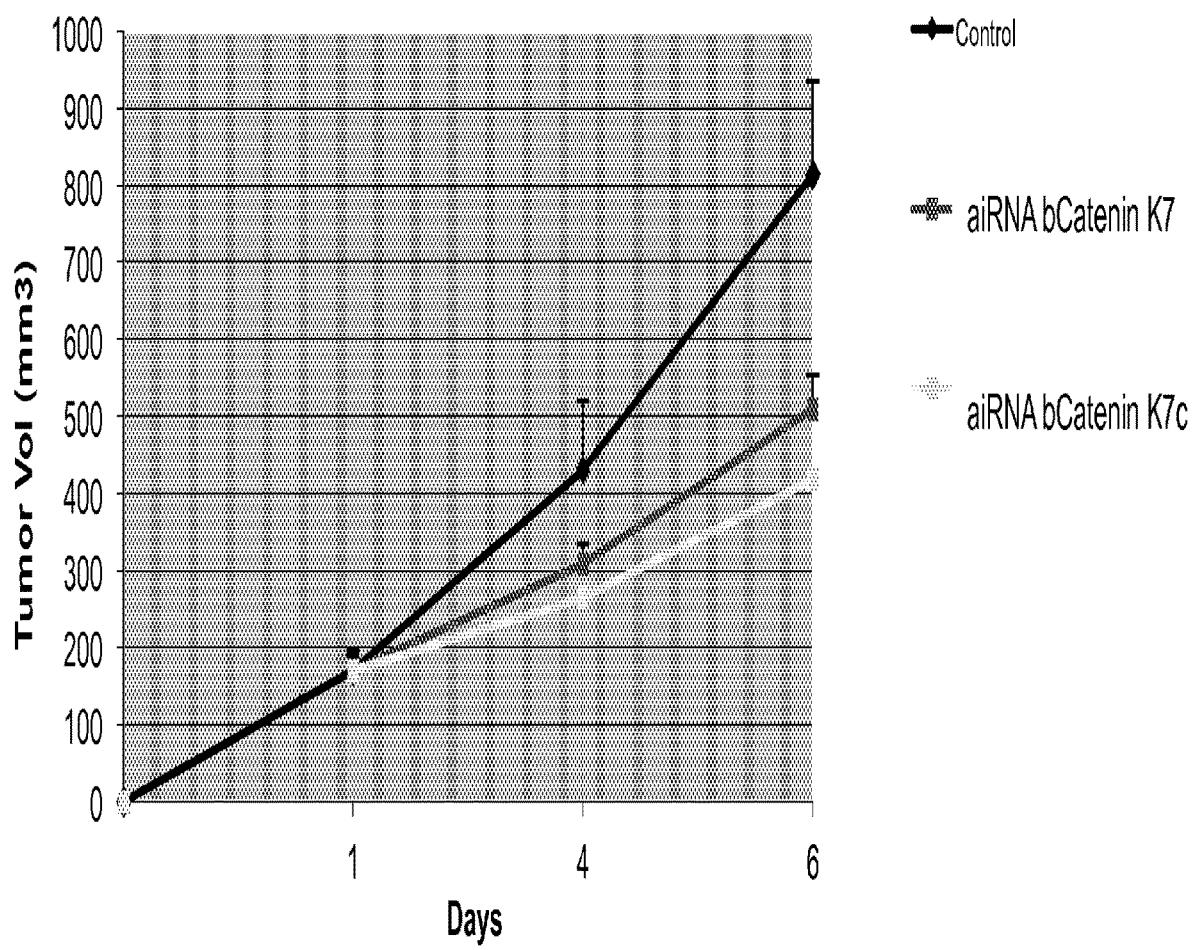
FIG. 31 illustrates data from in vivo studies for any therapeutic effect brought by the addition to cyclodextran in the K7 formulation.
Figure 32:
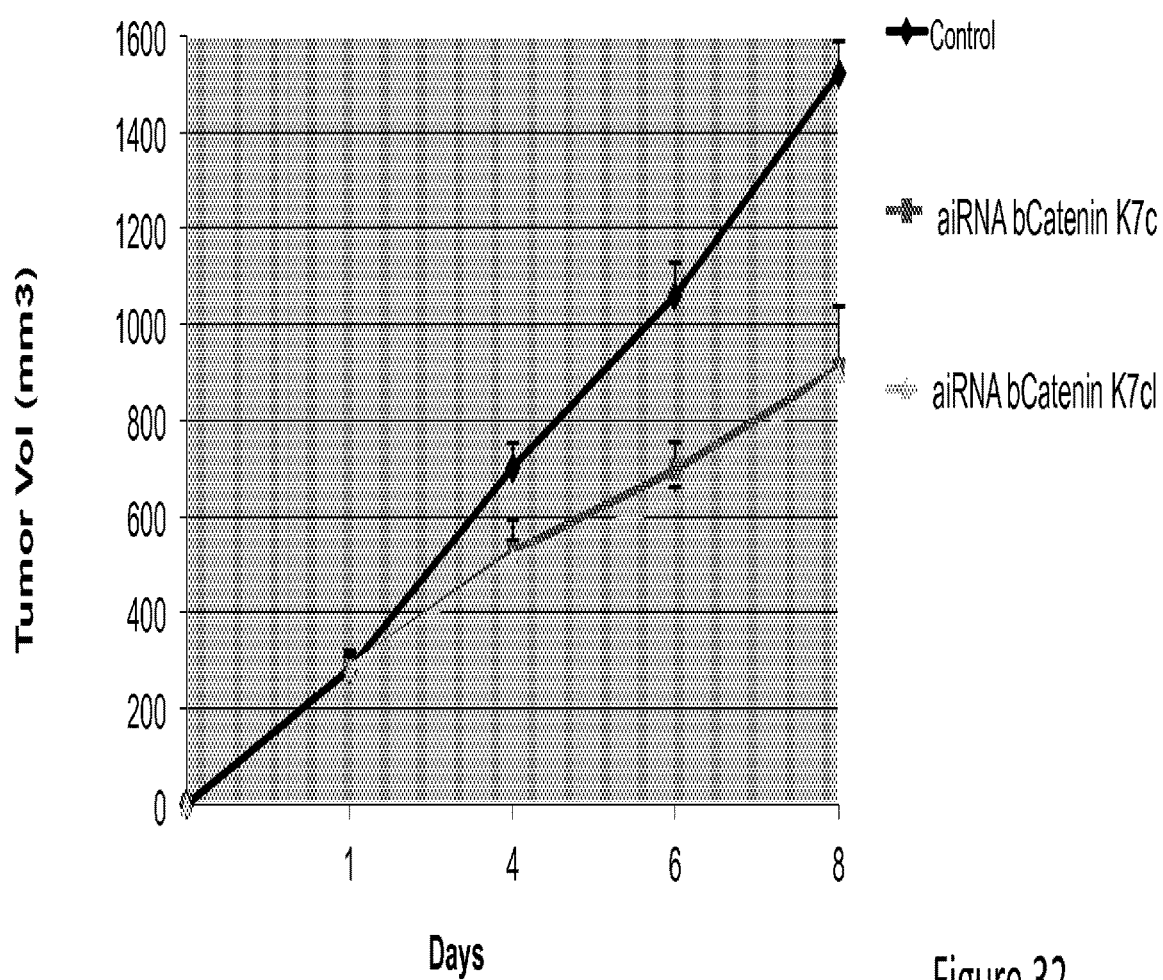
FIG. 32 illustrates data from in vivo studies for any therapeutic effect brought by the addition to cyclodextran and LABRAFL® in the K7 formulation. 2'-O-Me-iRNAs were used here.

Further optimization of validated drug formulations were carried out using nanoparticles with a MgP core. As shown in FIGS. 30-32, adding cyclodextran (FIG. 31) with or without LABRAFIL® (FIG. 32) further improved pharmaceutical efficacy of a validated intravenous formulation that surrounds the nanoparticle core with a shell containing protamine and CREMOPHOR®.

All numbers expressing quantities of ingredients, reaction conditions, analytical results and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A pharmaceutical composition comprising nanoparticles, wherein at least a plurality of the nanoparticles each comprises:
 a core comprising a magnesium salt consisting of magnesium phosphate, and a medically useful agent comprising a ribonucleic acid (RNA), wherein the core is encapsulated by a shell comprising a nonionic surfactant and a protein,
 wherein the RNA comprises an asymmetric interfering RNA (aiRNA) or a small interfering RNA (siRNA),
 wherein the nonionic surfactant is 1,3-dichloropropan-2-yl carbamate (CAS Registry Number: 61791-12-6),
 wherein the protein is protamine or histone, and
 wherein the nanoparticle has an average diameter of no more than about 50 nm.

2. The pharmaceutical composition of claim 1, wherein the nanoparticle does not include calcium phosphate.

3. The pharmaceutical composition of claim 1, wherein a plurality of the nanoparticles do not aggregate in aqueous solution.

4. The pharmaceutical composition of claim 1, wherein the nanoparticle has an average diameter that is no more than about 35 nm.

5. The pharmaceutical composition of claim 1, wherein the nanoparticle has an average diameter that is no more than about 20 nm.

6. The pharmaceutical composition of claim 1, further comprising a pharmaceutically acceptable excipient, carrier or diluent.

7. A pharmaceutical composition comprising nanoparticles,
 wherein at least a plurality of the nanoparticles each comprises:
 a core comprising an inorganic magnesium salt consisting of magnesium phosphate, and a medically useful agent comprising an RNA interfering (RNAi) molecule, wherein the core is encapsulated by a shell,
 wherein the RNAi molecule is an asymmetric interfering RNA (aiRNA) or a small interfering RNA (siRNA),
 wherein the shell comprises protamine and 1,3-dichloropropan-2-yl carbamate (CAS Registry Number: 61791-12-6).

8. The pharmaceutical composition of claim 7,
 wherein the shell further comprises an ingredient selected from the group consisting of cyclodextrin, 2-[1,3-bis(2-hydroxyethoxy)propan-2-yloxy]ethanol (CAS Registry Number: 62563-68-2), cholesterol and a targeting ligand.

9. The pharmaceutical composition of claim 7,
 wherein the shell further comprises cyclodextrin and 2-[1,3-bis(2-hydroxyethoxy)propan-2-yloxy]ethanol (CAS Registry Number: 62563-68-2).

10. The pharmaceutical composition of claim 7, wherein the nanoparticle does not include calcium phosphate.

11. The pharmaceutical composition of claim 7, wherein the aiRNA or siRNA is a modified aiRNA or modified siRNA.

12. The pharmaceutical composition of claim 7, further comprising a pharmaceutically acceptable excipient, carrier or diluent.

13. A nanoparticle comprising:
 a core comprising an inorganic magnesium salt, and a medically useful agent comprising an RNA interfering (RNAi) molecule, wherein the core is encapsulated by a shell,
 wherein the RNAi molecule is an asymmetric interfering RNA (aiRNA) or a small interfering RNA (siRNA),
 wherein the shell comprises protamine and 1,3-dichloropropan-2-yl carbamate (CAS Registry Number: 61791-12-6).

14. The nanoparticle of claim 13, wherein the inorganic magnesium salt is magnesium phosphate.

15. The nanoparticle of claim 13, wherein the medically useful agent further comprises a deoxyribonucleic acid, a protein or peptide, or a small molecule.

16. The nanoparticle of claim 13, wherein the core further comprises an additive selected from the group consisting of a nucleic acid, a protein or peptide, an amino acid, a carbohydrate, and a small molecule.

17. The nanoparticle of claim 13, wherein the shell further comprises an ingredient selected from the group consisting of cyclodextrin, 2-[1,3-bis(2-hydroxyethoxy)propan-2-yloxy]ethanol (CAS Registry Number: 62563-68-2), cholesterol and a targeting ligand.

18. The nanoparticle of claim 13, wherein the shell further comprises cyclodextrin and 2-[1,3-bis(2-hydroxyethoxy)propan-2-yloxy]ethanol (CAS Registry Number: 62563-68-2).

19. The nanoparticle of claim 13, wherein the nanoparticle does not include calcium phosphate.

20. The nanoparticle of claim 13, wherein the aiRNA or siRNA is a modified aiRNA or modified siRNA.

21. A nanoparticle comprising:
 a core comprising an inorganic magnesium salt, and a medically useful agent comprising an RNA interfering (RNAi) molecule, wherein the core is encapsulated by a shell,
 wherein the RNA comprises an asymmetric interfering RNA (aiRNA) or a small interfering RNA (siRNA),
 wherein the shell comprises histone and 1,3-dichloropropan-2-yl carbamate (CAS Registry Number: 61791-12-6).

22. The nanoparticle of claim 21, wherein the inorganic magnesium salt is magnesium phosphate.

23. The nanoparticle of claim 21, wherein the nanoparticle does not include calcium phosphate.

24. The nanoparticle of claim 21, wherein the aiRNA or siRNA is a modified aiRNA or modified siRNA.

25. The nanoparticle of claim 21, wherein the shell further comprises an ingredient selected from the group consisting of a ligand, an amino acid, a carbohydrate and a nucleic acid.

* * * * *